United States Patent
Diwan et al.

(10) Patent No.: US 8,173,764 B2
(45) Date of Patent: May 8, 2012

(54) SOLUBILIZATION AND TARGETED DELIVERY OF DRUGS WITH SELF-ASSEMBLING AMPHIPHILIC POLYMERS

(75) Inventors: Anil Diwan, West Haven, CT (US); Ann Louise Onton, Fairfield, CT (US); Jayant G. Tatake, Sandy Hook, CT (US)

(73) Assignee: AllExcel Inc., West Haven, CT (US)

( * ) Notice: Subject to any disclaimer, the term of this patent is extended or adjusted under 35 U.S.C. 154(b) by 262 days.

(21) Appl. No.: 12/223,052

(22) PCT Filed: Jan. 19, 2006

(86) PCT No.: PCT/US2006/001820
§ 371 (c)(1),
(2), (4) Date: Jun. 17, 2010

(87) PCT Pub. No.: WO2007/084126
PCT Pub. Date: Jul. 26, 2007

(65) Prior Publication Data
US 2010/0260743 A1    Oct. 14, 2010

(51) Int. Cl.
*C08G 63/02*   (2006.01)
*C08G 63/00*   (2006.01)

(52) U.S. Cl. ...... 528/271; 435/612; 435/6.13; 536/22.1; 536/24.3; 528/272

(58) Field of Classification Search ................ 435/6.12, 435/6.13; 536/22.1, 24.3; 528/271, 272
See application file for complete search history.

(56) References Cited

U.S. PATENT DOCUMENTS

| | | | |
|---|---|---|---|
| 5,919,442 A | 7/1999 | Yin et al. | |
| 6,322,805 B1 | 11/2001 | Kim et al. | |
| 6,399,700 B2 | 6/2002 | Mayes et al. | |
| 6,521,736 B2 | 2/2003 | Watterson et al. | |
| 6,730,334 B2 | 5/2004 | Zhao | |
| 7,939,259 B2 * | 5/2011 | Kokoris et al. | 435/6.1 |
| 2003/0072734 A1 | 4/2003 | Detert et al. | |
| 2003/0180244 A1 | 9/2003 | Soane et al. | |
| 2004/0248842 A1 | 12/2004 | Wagner et al. | |
| 2006/0148982 A1 | 7/2006 | Uchegbu et al. | |
| 2006/0269479 A1 | 11/2006 | Colton et al. | |

FOREIGN PATENT DOCUMENTS

| | | |
|---|---|---|
| CA | 2377211 | 1/2001 |
| WO | WO 03/078489 | 9/2003 |

OTHER PUBLICATIONS

International Search Report in PCT/US06/01820, dated May 10, 2006, 1 page.

Cho et al., "Folate receptor-mediated intracellular delivery of recombinant caspase-3 for inducing apoptosis", J. of Controlled Release 2005, 108:121-131.

Park et al., "Folate-conjugated methoxy poly(ethylene glycol)/poly($\epsilon$-caprolactone) amphiphilic block copolymeric micelles for tumor targeted drug delivery", J. of Controlled Release, 109:158-168.

* cited by examiner

*Primary Examiner* — Terressa Boykin
(74) *Attorney, Agent, or Firm* — James P. Demers

(57) ABSTRACT

There are provided amphiphilic biodegradable copolymers comprising a hydrophilic backbone with pendant aliphatic groups as the hydrophobic component. The polymers form nanoscale molecular aggregates in aqueous environments, which have hydrophobic interiors that are capable of solubilizing insoluble organic compounds such as drugs, vitamins, dyes, and imaging agents. The polymers optionally feature reactive functional groups that provide attachment points for antibodies, ligands, and other targeting moieties useful for the targeted delivery of drugs and imaging agents.

32 Claims, 2 Drawing Sheets

SOLUBILIZATION AND TARGETED DELIVERY OF DRUGS WITH SELF-ASSEMBLING AMPHIPHILIC POLYMERS

FIELD OF THE INVENTION

The present invention relates to the fields of amphiphilic polymers, and specifically to biocompatible micelle-forming comb-type polymers. The invention also relates to the fields of drug solubilization and targeted drug delivery.

BACKGROUND

Amphiphilic block copolymers comprising a hydrophobic block and a hydrophilic block have been well studied in recent years, because of their capacity for self-assembly into a variety of nanostructures as the surrounding solvent is varied. See Cameron et al., Can. Chem./Rev. Can. Chim. 77:1311-1326 (1999). In aqueous solutions, the hydrophobic compartment of an amphiphilic polymer has a tendency to self-assemble in order to avoid contact with water and to minimize the free interfacial energy of the system. At the same time, the hydrophilic blocks form a hydrated "corona" in the aqueous environment, and so the aggregates maintain a thermodynamically stable structure. The result is a stable, latex-like colloidal suspension of polymer aggregate particles having hydrophobic cores and hydrophilic coronas.

Comb-type amphiphilic co-polymers differ from block co-polymers in that the backbone is largely hydrophobic or hydrophilic, with polymer chains of opposite polarity pendant from the backbone rather than incorporated into it. Comb-type copolymers have been prepared with hydrophobic backbones and hydrophilic branches (Mayes et al., U.S. Pat. No. 6,399,700), and also with hydrophilic backbones and hydrophobic branches (Watterson et al., U.S. Pat. No. 6,521,736). The former were used to provide multivalent presentation of ligands for cell surface receptors, while the latter were used to solubilize drugs and deliver them to cells.

Amphiphilic polymer aggregates have been studied as carriers for solubilizing insoluble drugs, targeted drug delivery vehicles, and gene delivery systems. They have a more stable structure than conventional low-molecular-weight micelles, due to chain entanglement and/or the crystallinity of the interior hydrophobic region. The polymeric nature of the vehicle renders the aggregates relatively immune to the disintegration that ordinary liposomes suffer when diluted below their critical micelle concentration. They also have an advantage over traditional liposomal drug delivery compositions in that the absence of a bilayer membrane enables them to more readily fuse with cell membranes and deliver their payload directly to the cell.

Due to the excellent biocompatibility poly(ethylene glycol) (PEG), and the apparent ability of PEG-coated "stealth" particles to evade the reticuloendothelial system, micelles, liposomes, and polymers incorporating PEG have been extensively considered as materials for drug delivery systems. There are many reports of the use of poly(ethylene glycol) (PEG) as the hydrophilic component of PEG-lipids (forming liposomes and micelles); see for example Krishnadas et al., Pharm. Res. 20:297-302 (2003). Self-assembling amphiphilic block copolymers, which self-assemble into the more robust "polymersomes", have also been investigated as vehicles for drug solubilization and delivery (Photos et al., J. Controlled Release, 90:323-334 (2003)). See also Gref et ed., Int. Symp. Controlled Release Mater. 20:131 (1993); Kwon et al., Langmuir, 9:945 (1993); Kabanov et al., J. Controlled Release, 22:141 (1992); Allen et al., J. Controlled Release, 63:275 (2000); Inoue et al., J. Controlled Release, 51:221 (1998); Yu and Eisenberg, Macromolecules, 29:6359 (1996); Discher et al., Science, 284:113 (1999); Kim et al., U.S. Pat. No. 6,322,805; Seo et al., U.S. Pat. No. 6,616,941 and Seo et al., European Patent No. EP 0583955. The use of poly(ethyleneimine) (PEI) in this capacity has also been reported, with a focus on delivery of oligonucleotides (Nam et al., U.S. Pat. No. 6,569,528; Wagner et al., U.S. Patent application publication No. 20040248842). In a similar vein, Luo et al., in Macromolecules 35:3456 (2002), describe PEG-conjugated polyamidoamine ("PAMAM") dendrimers suitable for delivery of polynucleotides.

In addition to the need to solubilize, distribute, and deliver drugs, there is a need for targeted drug delivery systems that home in specifically on a target tissue, tumor, or organ. This is usually accomplished by attachment of antibodies or other ligands with a specific affinity for cell walls at the target site. However, PEG lacks functional groups except at the ends of the polymer chains, and the majority of the terminal groups are inevitably taken up by bonds to the other block copolymer component. For this reason, attachment of targeting moieties such as antibodies or cell-adhesion molecules to PEG block copolymers is generally limited to the non-PEG block, which unfortunately is not the part of the copolymer that is normally exposed in the corona of the self-assembled aggregate.

The phase separation phenomenon which results in the self-assembly of block copolymers into polymer aggregates is readily reversible, and attempts have been made to increase the stability of the aggregates by cross-linking the hydrophobic core (see European Patent No. EP 0552802). Covalent attachment of the drug to the hydrophobic component of a block copolymer has also been attempted (Park and Yoo, U.S. Pat. No. 6,623,729; European Patent No. EP 0397307).

There remains a need for a drug delivery system that is stable, biocompatible, amenable to the attachment of targeting moieties to the exterior of the aggregates, and efficient at delivering drugs to the desired cellular targets.

SUMMARY OF THE INVENTION

The present invention provides biocompatible comb-type polymer molecules, comprising a hydrophilic backbone having branch-point moieties, and hydrophobic branches attached at these branch-point moieties. The invention provides aqueous suspensions of polymer aggregates formed from such polymers, and provides methods for solubilizing insoluble or sparingly-soluble organic compounds, such as drugs, dyes, vitamins, and the like, by incorporating such compounds in the hydrophobic cores of the polymer aggregates. The method for solubilizing a water-insoluble organic species in an aqueous solvent basically comprises contacting the water-insoluble organic species with a polymer of the invention in an aqueous or mixed-aqueous solvent.

In particular embodiments, the branch point moieties further comprise reactive functional groups capable of serving as attachment points for targeting moieties. In particularly preferred embodiments, targeting moieties such as ligands or antibodies are covalently attached to the branch-point moieties of the polymers of the invention, and a drug is incorporated into the core of the aggregates, so as to form a targeted drug complex.

The invention further provides methods for the preparation of the comb-type polymers, aggregates, and targeted drug complexes described herein. The polymers of the invention self-assemble into polymer aggregates that efficiently solubilize, distribute, and deliver drugs in vivo, are non-toxic and biocompatible, are stable, and are capable of bearing multiple cell targeting moieties on their exterior surfaces.

DETAILED DESCRIPTION OF THE INVENTION

Figure 1:
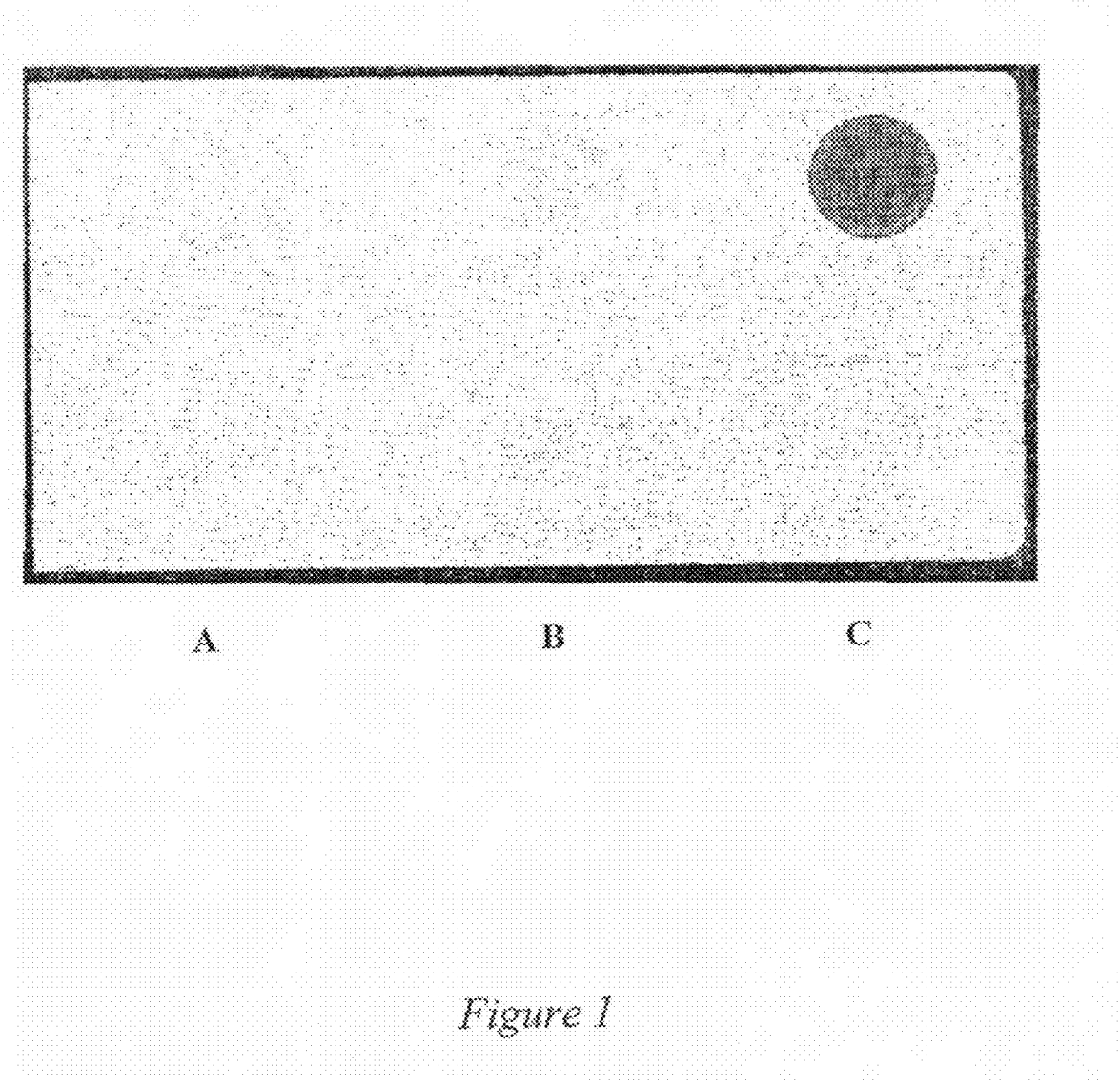
FIG. 1 shows 20 ul samples of saturated solutions of three lipophilic dyes (A, Sudan IV; B, dichlorofluorescein; C, spirit soluble Eosin Y) in deionized water, spotted onto a silica gel TLC plate. Upper row: with 50 mg/ml of the π-polymer of Example 1; lower row: without π-polymer.

The polymers of the invention, referred to herein as "π-polymers", have a comb-type architecture, with a backbone formed of alternating branch-point moieties B and hydrophilic, water-soluble polymer blocks A; and having a plurality of hydrophobic side chains C attached to each branch-point moiety. They consist essentially of the structure shown in Formula 1. The side chains C are relatively short, hydrophobic moieties, which may be aliphatic molecules, chains or oligomers. The value of p is ideally an integer, either 2, 3, or 4. In practice the side chains are most often introduced with less-than-perfect efficiency via chemical reactions, resulting in an average value of p for the polymer preparation as a whole that is not the intended integer. Non-integer average values can also be obtained by design, as discussed below. Thus, the average value of p in the polymers of the invention is greater than one and may be as high as four ($1 < p \leq 4$). In preferred embodiments, P ranges from about 2 to 4, and most preferably $1.5 < p \leq 2$.

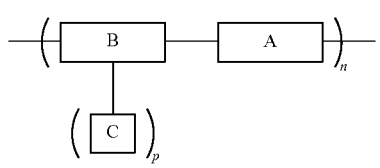

The backbone polymer block A is selected from hydrophilic and/or water-soluble polymer chains, including but not limited to poly(ethylene glycol), poly(propylene glycol), poly(ethylene imine), poly(vinyl alcohol), poly(vinylpyrrolidone), polysaccharides, and the like. Preferably, the polymer units A are poly(ethylene glycol) chains of formula —$(CH_2CH_2O)_m$— where m is between 1 and 10,000, preferably between 3 and 3,000. The terminal functional groups of the polymer chains have not been characterized, and are not relevant to the invention.

In the manufacture of poly(ethylene glycol) of various grades, it is known in the industry to couple a divalent linker moiety (e.g., bisphenol A diglycidyl ether) to two poly(ethylene glycol) chains, effectively doubling the molecular weight of the polymer while retaining a relatively narrow molecular weight range. The resulting "poly(ethylene glycol)" molecules are consequently interrupted at the midpoint of the polymer chain by the non-glycol linker moiety (see, e.g., the poly(ethylene glycol)-bisphenol A diglycidyl ether adduct, CAS registry No. 37225-26-6). Higher oligomers, i.e. those having three PEG chains separated by two bisphenol A diglycidyl ether moieties, are also known, see for example international patent application WO 00/24008. As used herein, therefore, the terms "poly(ethylene glycol)" and "poly (propylene glycol)" encompass poly(ethylene glycol) and poly(propylene glycol) polymer chains that incorporate non-glycol linker units, including but not limited to bisphenol A diglycidyl ether, bisphenol B diglycidyl ether, bisphenol S diglycidyl ether, hydroquinone diglycidyl ether, and the like. For purposes of this specification, any such linker moieties are not counted as "monomer units".

The polymer block A most preferably has an average length of between twenty and fifty monomer units. The polyethylene glycol chains may be end-substituted with functional groups suitable for use as linkers to other moieties, including but not limited to amino, mercapto, acrylate, acrylamide, maleate, maleimide, and the like, at one or both ends. The value of n ranges from 1 to 1000 and is preferably between 3 and 100. The overall molecular weight of the π-polymer may range from 1000 to 100,000 daltons or more; it is preferably above 2,000 daltons, and more preferably above 7,000 daltons.

Hydrophobic moieties C may be the same or different, and may be for example linear hydrocarbons (optionally substituted with one or more hydrophilic substituents), polycyclic hydrocarbons (optionally substituted with one or more hydrophilic substituents), hydrophobic amino acids, peptides and polymers. Suitable hydrophilic substituents include, but are not limited to, hydroxyl, ether, cyano, and amide functional groups. Specifically contemplated are $C_8$ to $C_{20}$ alkyl groups bearing ω-hydroxy, ω-cyano, ω-amido, or ω-alkoxy substituents. In this context, the term "substituent" includes the substitution of a heteroatom, such as O, N, or S, for a carbon atom in the hydrocarbon chain or ring system of the moiety C. Thus, ether and amide linkages, and heterocyclic rings, may be incorporated into C.

Hydrophobic moieties C are preferably relatively short ($C_8$-$C_{20}$) aliphatic chains, but may also be short oligomers. Suitable oligomers include oligo hydroxy acids such as poly (glycolic acid), poly(DL-lactic acid), poly(L-lactic acid), and copolymers of poly(glycolic acid) and poly(lactic acid)hydroxy acids, and poly(amino acids), poly(anhydrides), poly (orthoesters), and poly(phosphoesters), polylactones such as poly(epsilon-caprolactone) poly(delta-valerolactone) poly (gamma-butyrolactone) and poly(beta-hydroxybutyrate). C moieties may also be selected from hydrophobic molecules, such as cholesterol, cholic acid, lithocholic acid, hydrophobic peptides, and the like. The molecular weight of each moiety C is greater than 40, preferably between 50 and 1,000, and most preferably between 100 and 500. In general, any moiety C which is not appreciably soluble in water when in the molecular form C—H is thought to be suitable for use in the present invention.

It is a distinguishing feature of the comb polymers of this invention that the side chains C are not regularly and uniformly distributed along the polymer chain, but rather occur in clusters $[C]_p$. These clusters are spaced more or less regularly along the polymer chain, depending on the degree of monodispersity of the polymer units A. Thus, the distance between two side chains C attached to a common branching moiety B is different from the distance between two side chains attached to different branching moieties.

In a second embodiment of the invention, the branch-point moieties B further comprise one or more reactive functional groups X, and the polymers consist essentially of the structure shown in Formula 2.

$$\left( \begin{array}{c} (X)_r \\ B \\ (C)_p \end{array} - A \right)_n \quad 2$$

In Formula 2, the individual reactive groups X may be the same or may be different from one another, and may optionally be blocked or protected as may be necessary during assembly of the polymer 2. The average value of r will range from 0 (no X groups) to about 4. Typically, the reactive groups will be selected from functional groups known in the art to be useful for forming covalent linkages between molecular species. The groups X serve as attachment points for drug molecules, tissue- or cell-targeting moieties, virus-targeting moieties, or matrix attachment moieties (such as for the purpose of coating the surface of a stent or other medical device). In certain embodiments, there may be a single attachment point X. In other embodiments, there may be three or four different types of reactive groups. The matrix attachment moiety may attach to a matrix via covalent bonds, specific non-covalent interactions (e.g., antibody-antigen, or non-specific interactions (e.g., via ionic pairing or "hydrophobic" interaction). Suitable reactive groups X include but are not limited to —OH, —NH$_2$, —SH, —CHO, —NHNH$_2$, —COOH, —CONHNH$_2$, haloacyl, acetoacetyl, —CN, —OCN, —SCN, —NCO, —NCS, and the like; reactive double bonds such as vinylic, acrylic, allylic, maleic, cinnamic, and the like, and groups with reactive triple bonds such as acetylenecarboxy and acetylenecarboxamido (suitable for Michael additions, Diels-Alder reactions, and free radical addition reactions).

Exemplary cell-targeting moieties include but are not limited to receptor-specific ligands, antibodies, and other targeting moieties, such as peptides possessing an Arginine-Glycine-Aspartic acid (RGD) amino acid sequence or a Tyrosine-Isoleucine-Serine-Arginine-Glycine (YISRG) motif; growth factors including epidermal growth factor, vascular endothelial growth factor and fibroblast growth factor; viral surface ligands such as sialic acid and N-acetylneuraminic acid derivatives; cell receptor ligands such as folate, methotrexate, pteroic acid, estradiol, estratriol, testosternone, and other hormones; mannose-6-phosphate, sugars, vitamins, tryptophan, and the like. Antibodies are preferably monoclonal antibodies directed at cell-specific surface antigens; suitable targeting moieties include not only complete antibodies but also antibody fragments containing the active antigen-binding sequences, such as Fab'2 fragments, Fab' fragments, or short chain peptide analogues of the active antigen binding sequences of such antibodies.

Examples of virus-targeting moieties include small molecule ligands that bind to a virus, such as aminoalkyladamantanes, Fuzeon™, PRO-542, BMS-488043, sialic acid, 2:deoxy-2,3-didehydro-N-acetylneuraminic acid, 4-guanidino-Neu5Ac2en (zanamivir), oseltamivir, RWJ-270201, and the like; oligopeptides, oligosaccharides, and glycopeptides that bind to viral surfaces, and antibodies and antibody fragments directed at virus-specific surface antigens. In preferred embodiments, the present invention provides π-polymers bearing ligands for viral neuraminidase or hemagglutinin. It is well-established that such polymers have antiviral properties in their own right; see for example T. Masuda et al., *Chemical & Pharmaceutical Bulletin* 51:1386-98 (2003); M. Itoh et al., *Virology* 212:340-7 (1995), and Reece et al., U.S. Pat. No. 6,680,054 (2004). The hydrophobic cores of the antiviral polymers and polymer aggregates of the present invention may optionally be loaded with one or more conventional antiviral drugs, which are advantageously released in the vicinity of the viral particle.

Other attachment groups of medical relevance may be small chemicals, peptides, antibodies or antibody fragments, enzymes, or active pharmaceutical ingredients, that may affect biological processes such as hormones or hormone agonists or antagonists, substances that interfere with virus binding, substances that interfere with cell cycle or cellular processes after intracellular entry, and the like. Cells of unicellular and multicellular organisms, including bacteria, fungi, higher animals, and plants, may be targeted. Biotin may be attached to the π-polymer and used as an attachment point for avidin- and streptavidin-coupled proteins, peptides, and other targeting or pharmacologically active agents, such as antibodies, growth hormones, imaging reagents, and the like "Matrix" refers to organic or inorganic materials, surfaces, and deposits, such as glass, silica or metal surfaces, extracellular matrix, protein deposits such as amyloid plaques of various kinds, cell surface, virus surface, and general homogeneous or heterogeneous surfaces that may or may not be well characterized, including prions.

Examples of glass or silica matrix attachment moieties include various halosilanes, alkoxysilanes, acylsilanes, as well as chemicals exhibiting such functional groups including polymers. Other attachment groups can be devised based on the particular physico-chemical characteristics of the matrix. Suitable attachment moieties, for example those used in the coating of stents, are known to those skilled in the art.

In a third aspect of the invention, the branch point moieties B are connected to other branch point moieties elsewhere in the polymer chain, so as to form a crosslinked hydrogel structure. Such crosslinking may be effected by reacting the polymer with multifunctional moieties that contain homofunctional or heterofunctional groups, at least one of which reacts with X or a reactive group on C located on a first branch point moiety, and at least one of which reacts with X or with a reactive functional group present on C at a second branch point moiety. Cross-linking may also be made via a link to the terminal functional groups of the polymer chain A. Such crosslinked polymers may optionally contain reactive functional groups suitable for attachment of drug molecules or targeting moieties.

The branch-point moiety B is typically derived from a multifunctional molecule having a plurality of reactive groups, two of which are suitable for attachment to the hydrophilic polymer unit A, and two of which are suitable for attachment of the hydrophobic moieties C. Moiety B may optionally have additional reactive groups X as described above.

Particularly preferred branch-point moieties are the conjugates of dithiothreitol (DTT), dithioerythritol (DTE), or 2,3-diaminobutane-1,4-dithiol with two molecules of maleic acid. The combination of this branch-point moiety with polyethylene glycol as the moiety A generates the polymer backbone of Formulas 3 and 3a

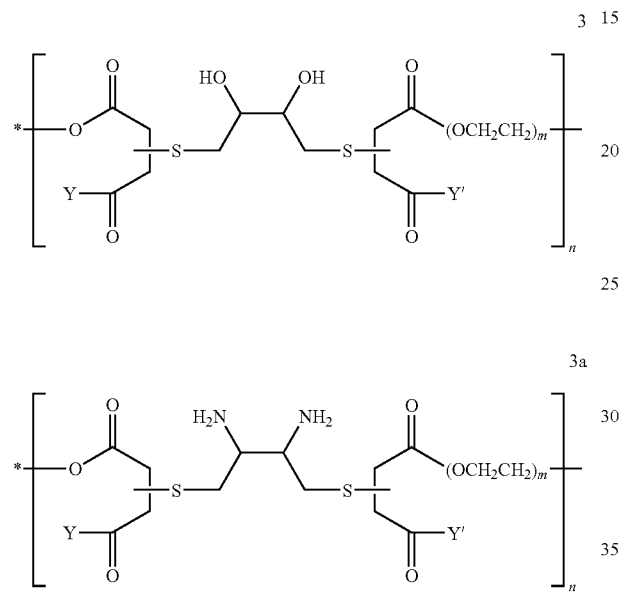

wherein Y and Y' may be the same or different, and are preferably selected from OH, $NH_2$, $ONH_2$, NHOH, and $NHNH_2$. In a preferred embodiment, the hydroxyl or amino groups of the dithiol are the reactive groups X, serving as attachment points for targeting or drug moieties, while the functional groups Y and Y' serve as attachment points for C moieties. Alternatively, the groups Y and Y' may serve as attachment points, while the hydroxyl or amino groups are used to attach the C moieties.

Formulas 3 and 3a are intended to convey that each sulfur atom may independently be attached alpha or beta to a PEG ester carbonyl group. The invention encompasses single isomer compositions as well as mixtures of regioisomers at one or both C—S bonds. Furthermore, due to the four asymmetric carbons in Formula 1, the invention encompasses all chiral, meso, and diastereomeric isomers and mixtures thereof.

The Diels-Alder adduct of acetylene dicarboxylic acid and a furan may also serve as a suitable branch point moiety. For example, the polyester 4 derived from PEG and acetylenedicarboxylic acid is known to undergo Diels-Alder reactions with furans (M. Delerba et al., *Macromol. Rapid Commun.* 18(8):723-728 (1997)).

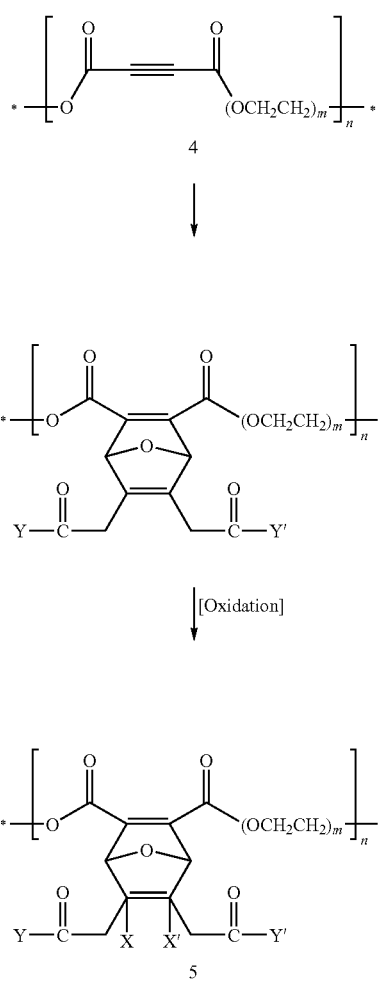

Thus, it may be subjected to a Diels-Alder reaction with a 3,4-disubstituted furan to generate a species such as 5, and polymer 5 can be modified by Hydroxylation or epoxidation to provide reactive groups (e.g., X and X' in Scheme 1).

Similarly, reaction of PEG with ethylenediamine tetraacetic acid dianhydride will provide a polyester of formula 6:

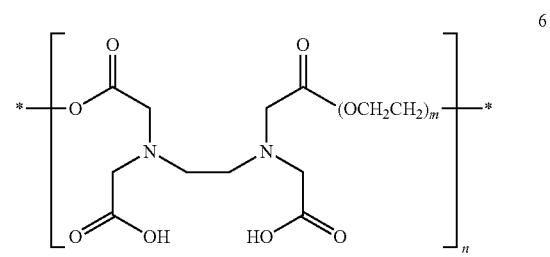

Other suitable branch point moieties may be derived from tartaric acid, acetylenedicarboxylic acid, nitrilotriacetic acid, 3,4,3',4'-diphenyl sulfone tetracarboxylic acid dianhydride, 3,4,3',4'-diphenyl ether tetracarboxylic acid dianhydride, pyromellitic dianhydride, alkanedithiols such as 1,2-ethanedithiol and 1,4-butanedithiol, bis(2-mercaptoethyl) ether, 2-mercaptoethylsulfide, dimercaptopropanol, dimercaptopurine, dimercaptothiadiazole, dimercaptosuccinic acid, benzenedimethanethiols, benzenedithiols, dihalogenated benzenedimethanethiols, dihalogenated 4,4'-thiobisbenzenethiol, and the like.

Where Y and Y' are OH, hydrophobic groups C may be linked to the polymer by amidation or esterification of the carboxylic acid groups. The hydrophobic groups C are preferably relatively small ($C_8$-$C_{20}$) and predominantly hydrocarbon moieties, and may be linear or branched or contain one or more rings. Examples include but are not limited to covalently attached dodecylamine, pentadecylamine, cholesterol, and cholic acid moieties. Although the polymers of the invention are represented, for convenience, as having at most two different hydrophobic side chains, is should be understood that mixtures of two or more hydrophobic compounds may be used to introduce a variety of hydrophobic side chains into a particular polymer.

As one specific example, a polymer of formula 2, where X=OH and r=2, was prepared by reacting a polyethylene glycol with maleic anhydride to form the polyester 7, followed by reaction with dithiothreitol to form 8. The acid 7 was then amidated with octadecylamine to form the desired comb polymer 9 (Scheme 2). The DTT-derived amide comb polymers represented by formula 9 are referred to herein as "π-Polymer A"; the specific polymer 9 in Scheme 2 would be designated "$C_{18}$-π-Polymer A".

Scheme 2

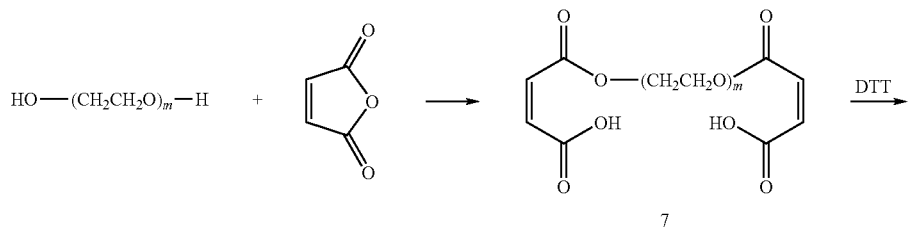

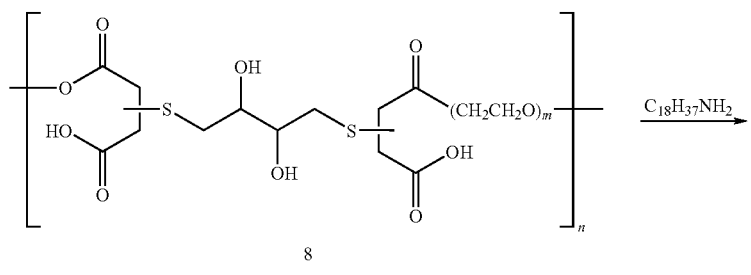

8

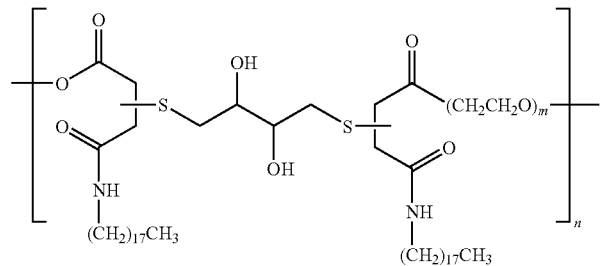

9

Substitution of 2,3-bis(t-butoxycarbonylamino)butane-1,4-dithiol (prepared by the method of DuPriest et al., U.S. Pat. No. 4,755,528) for dithiothreitol leads, after deprotection, to the corresponding amino-functionalized π-polymer 9 b (Scheme 3).

Scheme 3

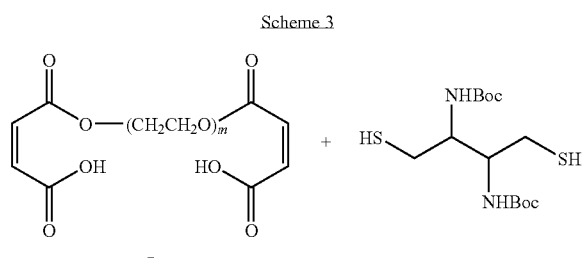

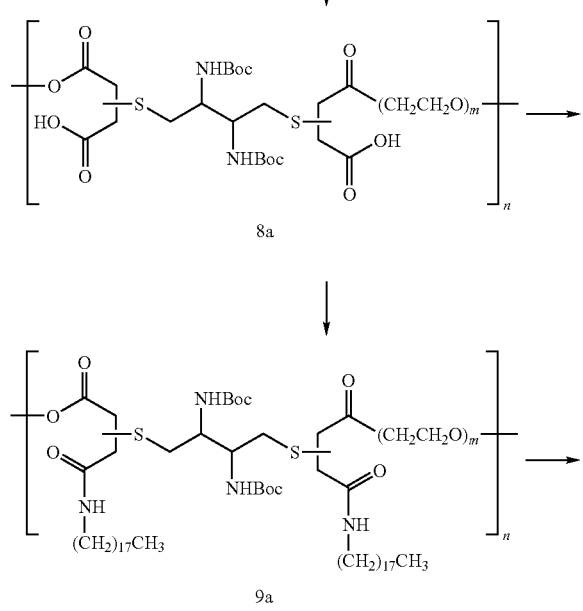

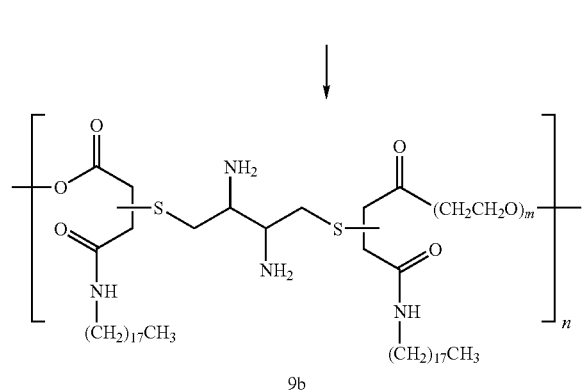

Scheme 4

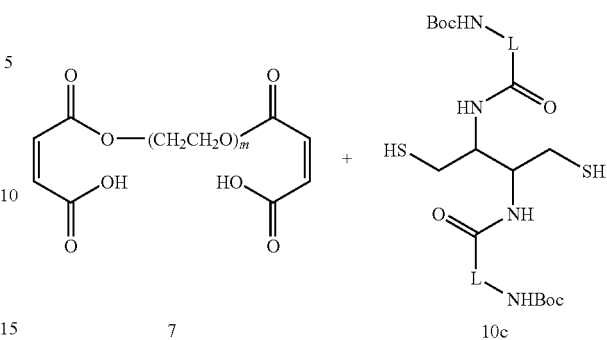

In other embodiments, a PEG polymer with terminal amino groups may be used to prepare examples having amide bonds between the A and B units, as shown in structures 10-14 below. Each of these polyamides may be derived via reaction of the PEG diamine $H2N-(CH_2CH_2O)_mCH_2CH_2-NH_2$ with the appropriate cyclic anhydride:

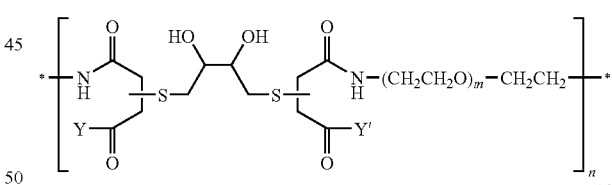

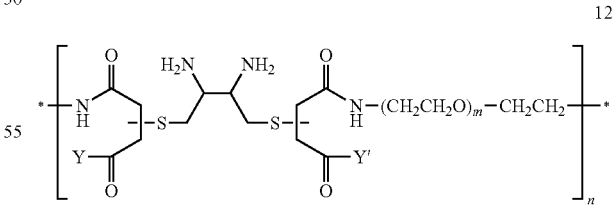

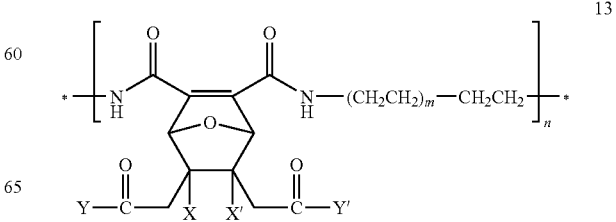

Use of the butanedithiol 10c likewise leads the polymers of general structure 9c, with spacer groups L in place for subsequent attachment of targeting moieties (Scheme 4). The spacer groups L may be any of the spacer groups known in the art for use in attaching ligands or labels to substrate molecules, including but not limited to $C_2$ to $C_{20}$ alkylene and oligo(ethylene glycol) spacers

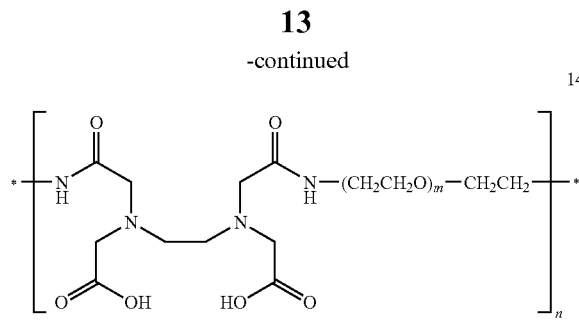

14

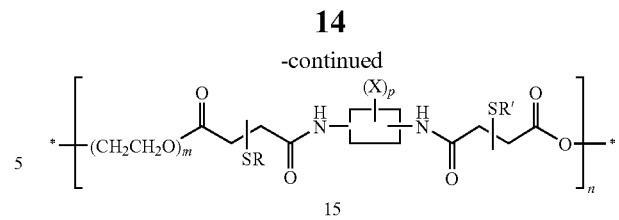

15

Under mild conditions, the above amido acids are the expected products. Upon heating, imide formation can be expected, leading to polymers with fewer reactive groups but still suitable for attachment of hydrophobic C moieties. Alternatively, the pendant side chains C can be added to the ends of the polymer A blocks, and the branch point moieties can come into existence at the time of polymerization (Scheme 5).

Certain of the π-polymers prepared as above possess reactive groups X suitable for further derivatization, to attach targeting moieties such as small molecules, peptides, nucleotides, sugars, antibodies, etc., or to effect crosslinking of the polymer chains via bifunctional or multifunctional crosslinking agents. In particular embodiments, partial derivatization of the reactive groups on the polymer chain is carried out to generate π-polymers having a variety of different reactive groups, which permits attachment of a variety of targeting and drug moieties to a single polymer chain. Thus, addition of a sub-stoichiometric amount of acryloyl chloride (or maleic Scheme 5

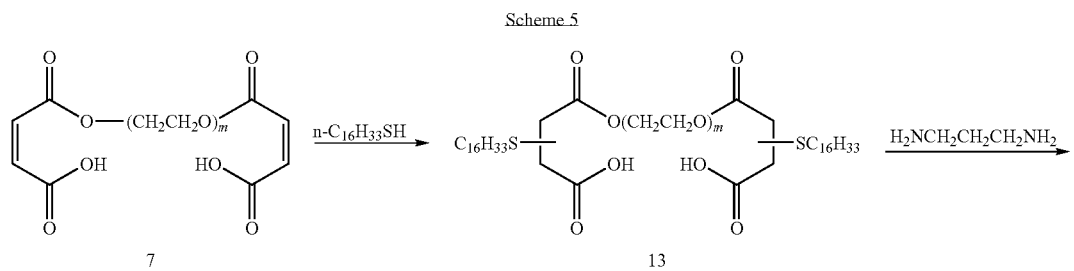

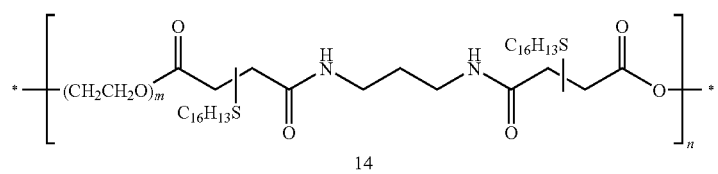

14

In addition to simple diamines such as 1,3-diaminopropane, as shown in Scheme 5, diamines having (optionally masked) reactive functional groups X may be employed, leading to polymers 15 suitable for attachment of targeting moieties (Scheme 6). In the formulae below, p may range from 0-4, and each X is independently the same or different from any other group X that may be present. A reactive group X need not be pendant, but may for example be an NH group within the chain of atoms that makes up the diamine, as in the monomer $H_2N-(CH_2)_3-NH-(CH_2)_3-NH_2$.

anhydride) to the π-polymer of Example 1 will provide a polymer with both acryloyl (or maleyl) groups and residual hydroxyl groups. Subsequent Michael addition of a sub-stoichiometric amount of a mercapto-carboxylic acid, for example $HS-(CH_2)_3-COOH$, would provide a polymer with hydroxyl, acryloyl, and carboxyl groups. Addition of cysteine introduces amino and carboxyl groups, in addition to any residual reactive groups left behind by sub-stoichiometric amounts of reagents.

Another approach to poly-functional π-polymers involves the deliberate omission of a fraction of the hydrophobic chains C. The π-polymer of Example 1, for example, can be prepared with unreacted carboxylic acid groups by the simple expedient of limiting the amount of pendant-forming alkylamine in the amidation step. Yet another approach is amidation with a mixture of amines, a fraction of which contains a reactive group X. Also, under appropriate conditions (excess maleic anhydride in Step A and excess DTT in Step B), a polymer preparation having a desired population of free thiol groups may be generated.

The π-polymer of Example 1 contains, by design, hydroxyl groups derived from the DTT moiety in the backbone, which serve as reactive groups X. Esterification of these groups with acryloyl chloride or methacryloyl chloride in aqueous media Scheme 6

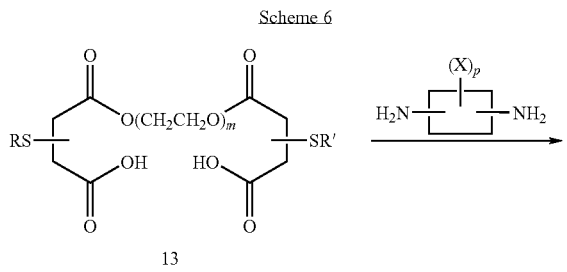

13 in the presence of a carbonate/bicarbonate buffer results in acryloyl substitution on the —OH groups. The acrylated polymer can be readily subjected to radical polymerization (with or without added radical monomer such as an acrylic compound or crosslinker such as a bisacrylic compound) to obtain hydrogels suitable for controlled drug delivery (acting as polymer depots or reservoirs) and for topical applications (such as skin patches or ointments).

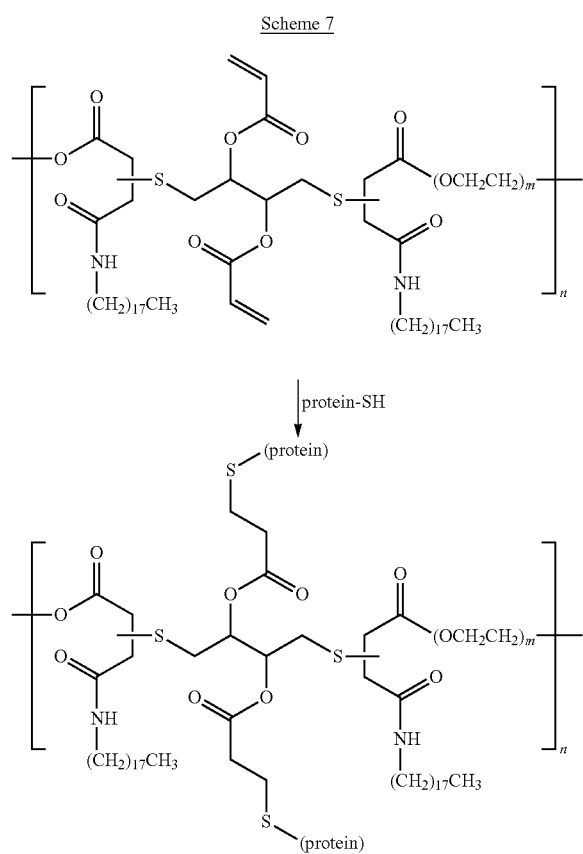

Scheme 7

The acryl group can also be subjected to a Michael addition, in particular, with a thiol, such as that of a cysteine residue in a protein, enzyme, peptide, antibody, Fab'2 fragment or Fab' fragment, or other targeting moiety (Scheme 7). A π-polymer possessing reactive hydroxyl groups, after drying, can also be esterified with maleic anhydride to attach the maleate group, a Michael acceptor, simultaneously generating a free carboxylic group. In the resulting polymer, the maleic double bond is available for a Michael addition, in particular, with a thiol, such as that of a cysteine residue in a protein, enzyme, peptide, antibody, Fab'2 fragment or Fab' fragment, or other targeting moiety. (Scheme 8), and the carboxyl group is available for coupling to amino groups of drugs or ligands, or the lysine residues in proteins and peptides.

A different moiety may further be attached to the newly introduced (or previously available) carboxylic group via amidation. Thus at least two different targeting moieties can be attached even under saturating reaction conditions (i.e. the moiety to be attached is present in stoichiometric excess).

Polymers bearing pendant carboxylate groups may be amidated with amines under typical coupling conditions, and they may also be converted to isocyanate groups via the Curtius rearrangement and then coupled with amines or alcohols to form ureas and carbamates, respectively. Such reactions may be used to introduce the hydrophobic groups C, or to attach targeting moieties.

Free amines can be introduced in the polymer by at least partially reacting one of the reactive groups with a diamine. The diamine must be chosen so that one of the amine groups is either protected or unreactive under the conditions of the reaction. The latter can frequently be accomplished by using ethylenediamine at a pH of about 7.5, since the pKa's of the two amino groups differ considerably. Preferably, this amidation is carried out as a separate step after the introduction of the hydrophobic pendant groups. A peptide or another molecule having a carboxylic group can then be attached by amidation at this free amine.

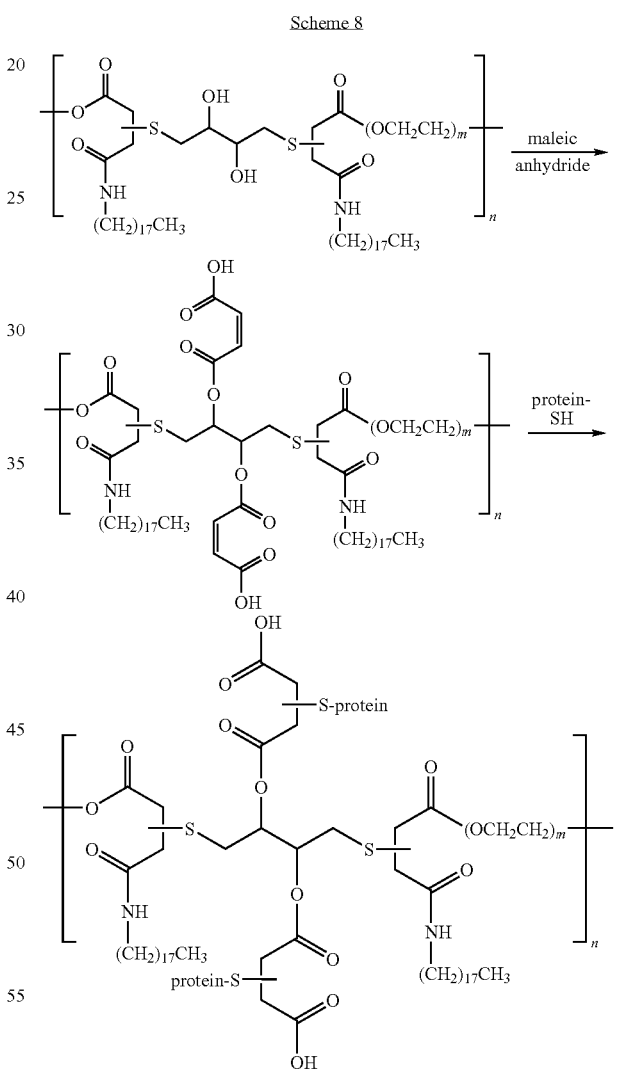

Scheme 8

Thus, even under saturating conditions, as many as three different peptides or other targeting moieties can be attached to the π-polymer: one via the thiol, one via the amine or hydroxyl, and one via the carboxylic acid group.

Hydroxyl and thiol groups can also be converted to primary amines by reaction with aziridine or a haloalkyl amine (such as bromoethylamine or chloroethylamine). Amidation with cysteamine will introduce a disulfide, which can be directly reacted with by the cysteine of a peptide or antibody to attach the peptide or antibody; or can be first reduced, e.g., with aminoethanethiol or DTT, for further reaction with a peptide or antibody.

By performing partial reactions, one can introduce additional reactive functional groups to a polymer of the invention, including but not limited to (1) thiol-reactive groups such as acrylic or maleic acid derivatives, (2) carboxylic-acid reactive groups such as amino or hydroxyl, (3) amine-reactive groups such as carboxyl, and (4) disulfide-reactive groups such as mercapto. The number of such added functional groups per polymer molecule may range from 1/r up to several multiples of r, depending on the reagent used and the quantity used.

Alternatively, two or more specific ligands can be attached to improve specificity of binding to say, a virus, or cell surface. Two or more specific ligands can also be used so as to cause an interaction between different cellular targets, for example, one ligand may target a virus particle, and another ligand may facilitate binding to a phagocyte, thereby bringing virus particle into proximity or contact with the phagocyte and promoting phagocytosis.

Such derivatization allows the attachment of three or more distinct targeting and/or therapeutic moieties to the polymer, through different functional group attachments (such as amine, carboxylate, and thiol). Thus, one may attach a tissue-specific targeting agent, an imaging agent, and a therapeutic agent to a single polymer chain, and subsequent self-assembly of the polymer will yield a targeted therapeutic whose distribution and efficiency of targeting can be monitored.

Attachment of ligands to the repeating units of the polymers of the invention affords multivalent display of the ligand on the polymer chain and on the nanoparticles surface. Multivalent display often leads to great increases in affinity for the target. For example, multivalent antibodies can be far more effective in clearance of their targets than the normal divalent antibodies. Carbohydrate-binding proteins and carbohydrates are known to be multivalent in nature, and ineffective if monovalent. Similarly, multivalent peptide and carbohydrate targeting moieties will be far more effective than the monomer alone. The increase in MW due to attachment to the polymer results in reduced renal clearance rates of peptides and other ligands. In addition, the PEG backbone affords to the peptide benefits similar to those of PEGylation, including evasion of immune surveillance.

Further, a multivalent targeting moiety will decorate a multivalent target (say, a virus particle) and neutralize it far more effectively than the Monomeric targeting moiety. The ability to display multiple (different) peptides in multivalent format will lead to enhanced specificity. For example, a truly HIV-specific (HIV virus-binding) polymer can be built by attaching a peptide corresponding to the CD4 binding region, and another peptide corresponding to the CCR-5 or CXCR-4 binding region of the virus, and possibly a third peptide corresponding to the other receptor (CXCR-4 or CCR-5 respectively). Such a polymer could completely mask the virus's binding regions and render the virus unable to attach to cells and thereby non-infective. In addition, the surfactant properties of the polymer would lead to destabilization of the virus structure itself upon binding. Instead of peptides, small molecules that interfere with the same binding patterns (CD4, CCR-5, CXCR-4) or a mixture of peptides and small molecules, preferably with complementary activities, can be employed. The resulting polymers will render any free virus ineffective, and thus may be ideal for stopping spread of infection, by using them as components of condom lubricants and the like. In addition, such polymers may be injected into patients to reduce the HIV burden.

Generally, when a polyfunctional reagent such as DTT is employed, there may be partial cross-linking of polymer chains via esterification of the carboxylic acid with DTT or similar side reactions. Secondary hydroxyl groups in the central region of the PEG chains, e.g. those associated with bisphenol A diglycidyl ether residues, may also contribute to cross-linking if they are present in the PEG starting material. The resulting crosslinked hydrogel structures are also useful materials. For example, by suitably increasing the extent of this crosslinking or by explicit crosslinking using alternative crosslinkers (such as bisoxiranes, for example), materials can be made that are flexible hydrogels which can serve as repository depots for drugs. By suitably modifying the materials (e.g. lower PEG length, greater open carboxylic groups, and incorporation of suitable acrylic groups) either linear or crosslinked hydrogel materials can be made that can serve as repositories that can be supported either immobilized on devices such as stents or absorbed in devices such as pads for adhesive patches or subdermal insertion patches. In general, such crosslinked materials will be suitable for controlled release rather than enhanced, targeted release.

The comb polymers of the invention are useful for solubilizing, in aqueous solvent systems, sparingly water-soluble materials. The method of solubilizing a substance in an aqueous solvent comprises contacting the sparingly-soluble substance with a comb-type polymer of the invention in the presence of water, so as to form a water-soluble complex of the substance and the polymer. Alternatively, the polymer and the substance to be solubilized may be combined in a two-phase aqueous-organic emulsion, and the organic solvent removed by evaporation. An exemplary process is described in U.S. Pat. No. 6,838,089, incorporated herein by reference. It is believed that in most cases, the polymer self-assembles into nanoparticles having the sparingly-soluble substance dissolved among the hydrophobic C chains that coalesce at the core of the particles, while the A blocks form a hydrophilic corona that sufficiently lowers the interfacial free energy to permit an aqueous suspension of the particles to remain stable.

In some cases, the sparingly-soluble substance may not entirely dissolve in the core, but may exist as a solid nanoparticle surrounded by and suspended in the C chains at the core of the particles. For the purposes of the present invention, this is a differences of degree, as the practice of the invention does not rely on any particular degree of mixing of the C chains with the sparingly-soluble substance. The substance may in some cases dissolve at the molecular level among the C chains, but in other cases it may exhibit any degree of phase separation from the C-chain environment. In some cases, it can be expected that the system will move from one state to the other as a function of temperature.

The solvating power of the hydrophobic core of the polymer particles can be modified by modifying the hydrophobic C moieties. Suitable modifications include but are not limited to the introduction of one or more hydrophilic substituents, such as hydroxyl, ether, amide, and cyano functional groups, in order to increase the polarity and/or polarizability of the hydrophobic core.

Sparingly-soluble materials that can be rendered soluble by these polymers include fat-soluble vitamins and nutrients, including but not limited to vitamins A, D, E and K, carotenes, cholecalciferol, and coenzyme Q; insoluble drugs such as docetaxel, amphotericin B, nystatin, paclitaxel, doxorubicin, epirubicin, rubitecan, teniposide, etoposide, daunomycin, methotrexate, mitomycin C, cyclosporine, irinotecan metabolite (SN-38), statins, and steroids; dyes, photodynamic agents, and imaging agents, and nucleic acids, nucleic acid analogues, and nucleic acid complexes. Nucleic acid analogues include species such as thiophosphates and peptide nucleic acids; nucleic acid complexes are ionic complexes of oligonucleic acids with a substantially charge-neutralizing amount of cationic or polycationic species.

For the purposes of this disclosure, a drug that is insoluble at neutral pH is considered "sparingly soluble", because there is in many cases a need for a neutral pharmaceutical composition. For example, ciprofloxacin is reasonably soluble in water at a pH below 4.5, but this pH can be highly irritating when the drug is formulated for ocular administration. A polymer of the present invention will solubilize ciprofloxacin in normal saline at pH 7. Also, for the purposes of this disclosure, "sparingly soluble" should be understood to refer to any substance whose solubility in an aqueous vehicle is such that an increase in solubility would yield an improved or more-useful composition. Thus, a drug that is moderately soluble, e.g. to the extent of 2 g/liter, is "sparingly soluble" if a unit dose for intravenous administration is 5 g.

As a result of the ability of the polymers of the invention to solubilize pharmacologically active species, the present invention also provides pharmaceutical compositions, which comprise one or more π-polymers of the invention in combination with a therapeutically effective amount of one or more pharmacologically active agents. The polymers of the invention can render effective what would otherwise be an ineffective amount of a pharmacologically active agent For purposes of this disclosure, therefore, a "therapeutically effective amount" is the amount of agent that renders the overall composition effective.

All patents, patent applications, and publications mentioned herein are hereby incorporated by reference in their entirety.

EXPERIMENTAL

1. General Procedures.

The invention also provides processes for the preparation of the comb polymers of the invention. Synthesis of these polymers is readily carried out by one skilled in the art of organic synthesis, by following the procedures described below. The key starting material is polyethylene glycol, which is preferably dried before use. This is conveniently done by stirring molten PEG under vacuum at an elevated temperature, until bubbles stop forming. This may take 8-12 hours, depending on the quality of the PEG. Once dried, the PEG can be stored under argon indefinitely. Commercially available industrial and research grades of PEG may be employed in making the polymers of the invention, for example the polydisperse "PEG 1500" of commerce having a molecular weight distribution of 1430-1570. Such material may incorporate bisphenol A diglycidyl ether, which introduces secondary hydroxyl groups at the center of the PEG chain. In order to ensure that the polymers of the invention have the most reproducible and consistent properties, the PEG is preferably free of bisphenol A, and of low dispersity. Most preferable are PEG polymers that are >95% monodisperse, such as are commercially available from Nektar Therapeutics (formerly Shearwater Polymers), Huntsville Ala., and Polypure AS, Oslo, Norway. An example of a particularly preferred PEG is "PEG-28" from Polypure, which is >95% $HO(CH_2CH_2O)_{28}H$, molecular weight 1252.

All reactions are carried out under an inert atmosphere such as nitrogen or argon, with magnetic or preferably mechanical stirring.

In step A, dry PEG is melted, and maleic anhydride (2 moles per mole of PEG) is added with stirring. The quantity of maleic anhydride should match the number of PEG terminal hydroxyl groups as closely as possible. A shortage of maleic anhydride will result in hydroxyl-terminated polymer chains, whereas an excess of maleic anhydride will consume thiol groups in the next step, leading to premature chain termination and terminal carboxyl groups. The reaction temperature is not critical, and the process can conveniently be carried out at temperatures between 45° C. and 100° C. The preferred temperature of the reaction is between 65° C. and 90° C. If elevated temperatures are employed, the maleic anhydride tends to sublime, and steps should be taken to see to it that the maleic anhydride remains in solution. Minimizing headspace and submerging the reaction vessel in an oil bath are effective methods.

Depending on the temperature selected, the reaction may be completed in 2 hours or less or can be conducted overnight. The reaction may be monitored by TLC on silica gel plates, and is continued until after the disappearance of the maleic anhydride. Visual contrast, UV, and iodine staining can all be used to examine the TLC plates.

In step B, the crude PEG bis-maleate ester produced in step A is combined with dithiothreitol (DTT) and N,N,N',N'-tetramethylethylenediamine (TEMED) (with added water, if necessary for fluidity), and the mixture stirred at 70° C. The reaction is complete within 30 min, as indicated by the rapid increase in viscosity. The molecular weight of the product will be reduced if more or less than the optimal amount of DTT is employed. The molecular weight of the product can also be reduced, if desired, by replacing TEMED with a less effective tertiary amine base such as TEA.

In step C, sufficient water is added to the reaction mixture to reduce viscosity, and 0.1 mol N-hydroxysuccinimide (NHS) and 1.05 mol hexadecylamine per mol carboxylic acid groups in the polymer are added. (This amount of NHS appears to optimally minimize the extent of side-reactions.) An excess of N-(3-dimethylaminopropyl)-N'-ethylcarbodiimide (EDC) (1.4 mol EDC per mol of carboxylic acid groups) is then added in portions, with additional water as added as necessary to maintain stirring. The pH of the reaction mixture is maintained above 7, and preferably between 9- and 11, to optimize the reactivity of the alkylamine. With dodecylamine, this reaction can be conducted at about 40-45° C., whereas with octadecylamine, the temperature is ca. 55° C.-57° C. The reaction is followed by TLC until a constant level of left-over alkylamine is observed, typically after running overnight.

The reaction mixture is acidified to a pH from about 3.0 to about 4.5 and stirred at room temperature for about 24 hours to destroy unreacted. EDC, then titrated to a pH of 7.0 using 1N NaOH. The final reaction mixture is centrifuged at about 800×g for 1 to 3 hours, to remove solid contaminants and by-products.

After centrifugation, the supernatant can be chromatographed on a GPC column (Toyopearl™, Sephadex™, Sephacryl™, Biogel™, etc.). The π polymers are amphipathic materials, and will exhibit affinity for most GPC column packings, thus complicating the removal of contaminants. Alternatively, the polymer may be chromatographed on a large-pore hydrophobic interaction column (e.g., TOYOPEARL™ Phenyl 650C, Toshoh Biosciences, Montgomeryville, Pa., U.S.A.), eluting with a gradient of methanol in water. Preferably, the reaction mixture is dialyzed against several changes of acidified and neutral water to remove low-molecular-weight starting materials and reaction by-products.

The reaction mixture may also be extracted with butanone, isopropanol, butanol or other polar organic solvents to remove organic impurities, but substantial amounts of the amphiphilic polymer are lost to the extraction solvent. Preferably the reaction mixture is subjected to ultrafiltration using suitable membranes to fractionate the product into molecular weight grades, such as 5 kDa to 10 kDa; 10 kDa to 30 kDa, 30 kDa to 50 kDa, etc. depending upon the cutoff of the filtration membrane employed. An aqueous solution of the polymer may be subjected to dead end filtration as to produce a sterile or virus-free solution, depending upon the choice of filtration membrane or media.

2. Synthesis of π-Polymers

Example 1

PEG-Di(alkylamidosuccinyl)dithioether Medium Molecular Weight Polymer (C16-π-Polymer A)

Polyethylene glycol (PEG-1500, Sigma Chemical Co.) was dried under vacuum at 80° C. until bubbles stopped forming. (8-12 hours, depending on the quality of the PEG.) The dried PEG can be stored desiccated under argon indefinitely.

The dried PEG was melted under argon on an oil bath, and maleic anhydride (2 moles per mole of PEG, corrected for impurities) was added gradually with stirring. The mixture was stirred under argon at 90° C. Because maleic anhydride tends to sublime, the head space was minimized and the entire reaction vessel was kept at the reaction temperature. Any condensed maleic anhydride on the vessel walls was scraped back into the reaction mixture. The progress of the reaction was monitored by TLC on silica gel plates, using ethanol and hexane as solvents separately, with UV visualization and iodine staining. The reaction was continued for one hour past the disappearance of the maleic anhydride.

The crude PEG dimaleate was diluted with two volumes of water. A solution of dithiothreitol (DTT, 1.01 equivalents per equivalent of PEG) and N,N,N',N'-tetramethyl-ethylenediamine (TEMED, 1.02 equivalents) in water (2 volumes water per volume of TEMED) was then added to the reaction mixture with stirring. The reaction was stirred at 70° C. under argon for 2.5 hrs, left at room temperature overnight, and then stirred again at 70° C. for 2 hours. The reaction was monitored by TLC and was judged complete upon complete disappearance of the DTT.

Water was added to the above reaction mixture to reduce the viscosity, until the mixture could be stirred (at ca. 25% solids), the mixture was stirred at 65° C. under argon, and N-hydroxysuccinimide (0.1 mol per mol carboxylic acid groups in the PEG-dimaleate-DTT polymer) was added, followed by hexadecylamine (1.05 mol per mol carboxylic acid groups in the polymer) and N-(3-dimethylaminopropyl)-N'-ethylcarbodiimide (EDC, 0.56 mol per mol carboxylic acid groups in the polymer). The mixture was stirred under argon for 1 hour and a second portion of EDC (0.56 mol per mol carboxylic acid groups in the polymer) was added. After another hour, a third portion of EDC (0.28 mol per mol carboxylic acid groups in the polymer, for a total of 1.4 mol EDC per mol of carboxylic acid) was further added to account for loss of EDC to hydrolysis. Additional water was added as necessary to maintain fluidity, as the added solids made the suspension difficult to stir, and the pH was maintained between 8 and 10 by addition of 1N NaOH as needed. The mixture was stirred at 65° C. under argon overnight, monitored by TLC (silica with ethanol) until the alkylamine appeared to have reached a steady concentration, and was then stirred for an additional 4 h. The reaction mixture was then acidified with 1N HCl to a pH of about 4.5, stirred for 24 h to destroy unreacted EDC, and adjusted to pH 7.0 by dropwise addition of 1N NaOH. With dodecylamine, this reaction was conducted at about 40-45 C, whereas with octadecylamine, the temperature was preferably 55-57° C.

The mixture was transferred to centrifuge bottles and spun in a benchtop centrifuge at about 800×g for 2 hours to separate residual solids. After centrifugation, the reaction mixture was extracted with isopropanol to remove organic impurities. Ultrafiltration is preferred as an alternative to isopropanol extraction.

By this method, the following amino compounds are conjugated to the polymer:
Example 1a: undecylamine
Example 1b: octadecylamine
Example 1c: 4-nonylbenzylamine
Example 1d: 3-[(4-phenoxy)phenyl]propylamine

Example 2

PEG-Di(alkylamidosuccinyl)dithioether High Molecular Weight Polymer

The procedure outlined in Example 1 was followed, except that 0.55 mol DTT and 0.55 mol TEMED per mol maleic anhydride were used. Vigorous stirring was necessary as the viscosity built up rapidly. It appeared that most of the reaction was complete within 5-10 minutes, followed by slow completion over the next 4 hours as the temperature was raised from 55° C. to 80° C.

Example 3

PEG-Di(alkylamidosuccinyl)dithioether Polymer

The procedure outlined in Example 1 was followed, except that 1.5 mol dodecylamine per mol of carboxylic acid groups in the polymer was employed. N-hydroxysuccinimide (NHS, 1.0 mol per mol of carboxylic acid groups) and 1,1'-Carbonyldiimidazole (CDT, 3.0 mol per mol of carboxylic acid groups) were added, and the reaction was stirred at 80° C. for 4 hours and worked up as above.

By this method, the following amino compounds are conjugated to the polymer:
Example 3a: undecylamine
Example 3b: tetradecylamine
Example 3c: octadecylamine
Example 3d: dehydroabietylamine
Example 3e: cholesterol 2-aminoethyl ether
Example 3f: 10-phenoxydecylamine
Example 3g: sebacic acid hydrazide
Example 3h: oleic acid hydrazide
Example 3l: dehydroabietic acid hydrazide
Example 3j: cholic acid hydrazide
Example 3k: palmitic acid hydrazide

Example 4

PEG-co-(alkylamidosuccinate) Polymer

A solution of PEG (6.66 mmol) and triethylamine (2.32 ml, 16.65 mmol) in dry diethyl ether (10 ml) is cooled at 0° C. under argon and treated dropwise with methanesulfonyl chloride (1.03 ml, 13.32 mmol). Stirring is continued for 1 h at 0° C. and then at room temperature for 2 h. The ether is evaporated and dry acetone (15 ml) is added to the residue in order to precipitate the triethylamine hydrochloride, which is filtered from the solution. The filtrate is treated with lithium bromide (2.31 g, 26.64 mmol) and heated to reflux for 20 h. Then the mixture is diluted with hexane and filtered through a short column of silica (3 cm) covered with Celite™ (0.5 cm), and eluted with hexane. The filtrate is dried, filtered and evaporated to leave α,ω-dibromo-PEG an oil.

α,ω-Dibromo-PEG is reacted with one equivalent of 2,2-dibutyl-4,5-bis(methoxycarbonyl)-1,3,2-dioxastannolane by the method of Godjoian et al., *Tetrahedron Letters*, 37:433-6 (1996). The resulting dimethyltartrate-PEG polyether is saponified with KOH in methanol, and then amidated with dodecylamine or hexadecylamine as in examples 1 and 3 above, or with the amines in examples 3a-3k.

Example 5

PEG Copolymerization with EDTA Dianhydride

Dry PEG is reacted with ethylenediaminetetracetic acid dianhydride by the method described in Example 1, and is then amidated with dodecylamine as in Example 1 or hexadecylamine as in example 3, or with the amines in examples 3a-3k.

In the same manner, the following dianhydrides are co-polymerized with PEG and subsequently amidated:
Example 5a: Naphthalenetetracarboxylicdianhydride
Example 5b: Perylenetetracarboxylicdianhydride
Example 5c: Benzophenonetetracarboxylicdianhydride
Example 5d: 4,4'-(Hexafluoroisopropylidene)diphthalic anhydride
Example 5e: Butane Tetracarboxylic Acid Dianhydride
Example 5f: Bicyclo(2,2,2)oct-7-ene-2,3,5,6-tetracarboxylic dianhydride
Example 5g: Diethylenetetramine Pentaacetic Acid Dianhydride
Example 5h: 3,4,3',4'-Diphenylsulfone tetracarboxylic acid dianhydride
Example 5I: 3,4,3',4'-Diphenyl ether tetratarboxylic acid dianhydride
Example 5j: Pyromellitic dianhydride Example 6A PEG-Diamine Co-polymer with Pendant Thioethers PEG dimaleate, prepared as in Example 1, is reacted with dodecanethiol (two equivalents per equivalent of PEG dimaleate) using the same procedure as used for DTT in Example 1. No dilution is necessary, as no polymerization takes place, and the reaction is conducted in molten PEG-dimaleate. The TEMED catalyst is added and then the thiol is added. The reaction is followed by the disappearance of starting materials, using TLC. Temperatures up to the point where the loss of alkylthiol by vaporization becomes significant can be employed (up to ca. 100° C.). A slight excess of alkylthiol may be employed to fully saturate the maleic groups. The excess allylthiol is driven off at the end of reaction by sparging with nitrogen or argon, and/or heating under vacuum, until none is detected by odor or by TLC.

By this method, the following thiols may be conjugated to PEG dimaleate:
Example 6Aa: mercaptosuccinic acid di-t-butyl ester
Example 6Ab: tetradecanethiol
Example 6Ac: hexadecanethiol
Example 6Ad: 2-mercaptoethanesulfonic acid
Example 6Ae: 3-mercaptopropanesulfonic acid
Example 6Af: 6-mercaptohexanoic acid t-butyl ester
Example 6Ag: 4-mercaptobenzoic acid t-butyl ester
Example 6Ah: mercaptoacetic acid t-butyl ester
Example 6Ai: 4-(t-butoxycarbonylamino)butanethiol
Example 6Aj: 3-(t-butoxycarbonylamino)benzyl mercaptan
Example 6Ak: 4-decylbenzyl mercaptan Thiols having reactive functional groups are suitable for attachment of C chains, and/or the reactive functional groups may serve as attachment points (X) for targeting moieties.

Example 6B

PEG-Diamine Co-polymer with Pendant Thioethers

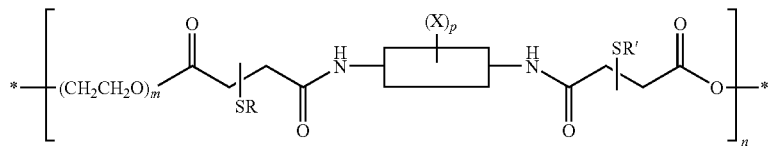

The thiol adduct obtained in Example 6A is amidated with 1,4-diaminobutane (one equivalent of diamine per two COOH groups), using the same procedure used for dodecylamine in Example 1, with dilution with water is as necessary to maintain the fluidity of the reaction mixture. Additional aliquots of EDC are added as necessary to ensure complete polymerization. By this method, the thiol adducts of Example 6A and 6Aa through 6Ak are converted to a PEG-diaminobutane polyamide.

By this method, the following diamines may be converted to a PEG polyamide (BOC=t-butoxycarbonyl):
Example 6Ba: 2-(O-BOC)-1,3-diamino-2-propanol
Example 6Bb: N',N"-di(BOC) hexaethylene tetraamine
Example 6Bc: N',N"-di(BOC) spermine
Example 6Bd: N'-BOC spermidine
Example 6Be: N',N",N'''-tri(BOC) pentaethylene hexamine
Example 6Bf: agmatine
Example 6Bg: lysine t-butyl ester
Example 6Bh: 1,6-diaminohexane
Example 6Bi: 1,4-phenylenediamine
Example 6Bj: 1,3-phenylenediamine
Example 6Bk: 1,4-diaminobutane-2,3-diol acetonide

Example 7

PEG-Di(alkylsuccinate)dithioether

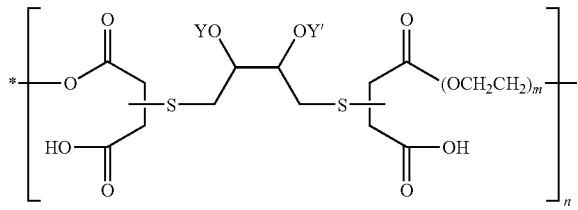

The 2,3-bis-O-hexadecyl ether of DTT (meso-2,3-bis(hexadecyloxy)butane-1,4-dithiol) is prepared by a modification of the procedure of S. Sasaki et al., *Chem. Pharm. Bull.* 33(10):4247-4266 (1985). This is added to PEG-dimaleate by the method of Example 1.

By this method, the following ether dithiols are coupled to the PEG polymer:
- Example 7a: meso-2,3-bis(n-butoxy)butane-1,4-dithiol
- Example 7b: meso-2,3-bis(4-nonylphenylmethoxy)butane-1,4-dithiol
- Example 7c: meso-2,3-bis(biphenyl-4-methoxy)butane-1,4-dithiol
- Example 7d: 4,6-bis(decyloxy)benzene-1,3-dimethanethiol
- Example 7e: 4,5-bis(decyloxy)benzene-1,2-dimethanethiol
- Example 7f: 3,4-bis(decyloxy)thiophene-2,5-dimethanethiol

Example 8A

Substituted PEG Succinates

The method of Example 1 is followed, except that 2-dodecen-1-yl succinic anhydride is used in place of maleic anhydride. The dodecenyl substituent provides the pendant C chains in the final polymer.

By this method the following substituted succinic anhydrides are esterified with PEG:
- Example 8Aa: isobutenylsuccinic anhydride
- Example 8Ab: 2-octene-1-yl succinic anhydride
- Example 8Ac: octadecenyl succinic anhydride
- Example 8Ad: 3-oxabicyclo-hexane-2,4-dione
- Example 8Ae: cyclohexanedicarboxylic anhydride
- Example 8Af: phthalic anhydride
- Example 8Ag: 4-decyl phthalic anhydride
- Example 8Ah: hexahydromethylphthalic anhydride
- Example 8Ai: tetrahydrophthalic anhydride
- Example 8Aj: norbornenedicarboxylic anhydride
- Example 8Ak: cantharidin
- Example 8Al: bicyclooctenedicarboxylic anhydride
- Example 8 Am: exo-3,6-epoxy-1,2,3,6-tetrahydrophthalic anhydride
- Example 8 An: S-acetyl mercaptosuccinic anhydride

Example 8B

PEG-Di(alkylamidosuccinyl)dithioether with Pendant Alkyl Groups

By the method of example 1, the substituted PEG succinates obtained as described in Examples 8A and 8Aa through 8 An are reacted with DTT.

By this method, the following dithiols are reacted with any of the substituted PEG succinates obtained as described in Examples 8A and 8Aa through 8 An:
- Example 8Ba: ethane-1,2-dithiol
- Example 8Bb: propane-1,3-dithiol
- Example 8Bc: butane-1,4-dithiol
- Example 8Bd: pentane-1,5-dithiol
- Example 8Be: hexane-1,6-dithiol
- Example 8Bf: 1,4-benzenedithiol
- Example 8Bg: 1,3-benzenedithiol
- Example 8Bh: 1,4-benzenedimethanethiol
- Example 8Bi: 1,3-benzenedimethanethiol
- Example 8Bj: 1,2-benzenedimethanethiol

Example 8C

PEG-Diamine Copolymer with Pendant Alkyl Groups

By the method of example 6B, the substituted PEG succinate obtained as described in Example 8A is co-polymerized with 1,4-diaminobutane.

By this method, the following diamines are co-polymerized with any of the substituted PEG succinates of Examples 8A and 8Aa through 8 An:
- Example 8Ca: 2O-BOC 1,3-diamino-2-propanol
- Example 8Cb: N',N'''-di(BOC) hexaethylene tetraamine
- Example 8Cc: N',N''-di(BOC) spermine
- Example 8Cd: N'-BOC spermidine
- Example 8Ce: N',N''',N''''-tri(BOC) pentaethylene hexamine
- Example 8Cf: agmatine
- Example 8Cg: lysine t-butyl ester
- Example 8Ch: 1,6-diaminohexane
- Example 8Ci: 1,4-phenylenediamine
- Example 8Cj: 1,3-phenylenediamine
- Example 8Ck: 1,4-diaminobutane-2,3-diol acetonide

Example 9

PEG Trans-esterification Using Substituted Acids

PEG ditosylate: To 1 mol of PEG (dissolved in DMF or melted as is) was added 2.1 mol of tosyl chloride (5% molar excess) while stirring under argon. To this reaction mixture was added 2.2 mol of tetramethyl ethylene diamine (TEMED). The reaction was then incubated at 45° C. for 2 h. The products were resolved using TLC in ethylacetate, toluene, or ethanol as TLC solvents. The PEG ditosylate may be extracted from the reaction mixture with toluene. Instead of toluenesulfonyl chloride, other sulfonylating agents such as mesyl chloride (see Example 4), triflic anhydride, or tresyl chloride may also be used (see U.S. patent application Ser. No. 10/397,332, Publication No. 20040006051).

Polyesterification of PEG ditosylate: To 1 mol of molten PEG-ditosylate, with stirring under argon, is added 1 mol of S,S'-didecyl-meso-2,3-dimercaptosuccinic acid and 2 mol of TEMED. DMF is added as necessary to maintain fluidity. The reaction mixture is heated to 80° C. and stirred for 24 h or until complete by TLC.

Example 10

PEG-Di(succinyl)-di-(O-Acylated)thioether Medium Molecular Weight Polymer (C16-π-Polymer B)

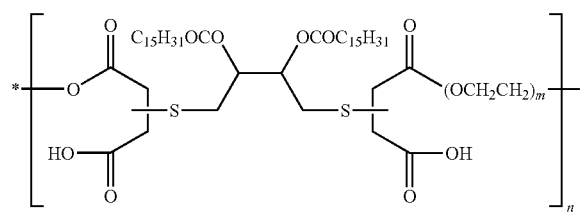

PEG-dimaleate (10.24 g, 6.1 mmols) prepared as in Example 1 was placed in a dry 125 ml flask and heated to 70° C. under argon to melt the PEG-dimaleate. To this molten material, with stirring, was added water (10 mL) and a solution of DTT (0.961 g, 6.168 mmols) and TEMED (0.723 g, 6.166 mmols) in water (3 mL). The solution was stirred at 70° C. for about 4 hr. Removal of water in vacuo gave the solid polymer in about 90% yield.

The dried polymer (5 g, 2.7 mmols) was heated to 70-90° C. under argon to melt it, and TEMED (0.635 g, 5.5 mmols) was added Palmitoyl chloride (1.689 g, 5.5 mmols) was added with stirring, and the mixture was stirred under argon overnight. (The ratio of polymer to acyl chloride can be varied to obtain degrees of substitution from 0-100% of stoichiometry.) Water was added to the reaction mixture to isolate the "C16-π-Polymer B".

By this method the following acids are esterified with the hydroxyl groups of the di(succinyl)PEG-DTT copolymer:
Example 10a: Oleic acid
Example 10b: Cholesteryl Succinate
Example 10c: Biphenyl-4-carboxylic acid
Example 10d: 4-Octylphenylacetic acid
Example 10e: Hexadec-6-ynoic acid As an alternative to the use of acid halides, the DTT-derived hydroxyl groups of π-polymers may also be activated with 1,3-bis(2,2-dimethyl-1,3-dioxolan-4-ylmethyl)carbodiimide (BDDC) and coupled directly with carboxylic acids; see *Handbook of Reagents for Organic Synthesis, Reagents for Glycoside, Nucleotide, and Peptide synthesis*, Ed. David Crich, Wiley, 2005 p 107-108 and references therein).

Example 11

Dimaleate of C16-π-Polymer A

Polymer A dimaleates are prepared by reacting maleic anhydride with Polymer A hydroxyl groups. The activated double bond introduced may be used to add thiol-containing ligands to the polymer. The ratio of Polymer A to maleic anhydride can be varied to obtain substitutions varying from 0-100% of full stoichiometric esterification.

C16-π-Polymer A (2 g) and maleic anhydride (0.85 g) were ground in a dry mortar and transferred to a 50 mL round bottom flask. The flask was heated at 90° C., under argon, for 2-3 hr with stirring. The solid reaction mixture was then transferred with help of water to a dialysis bag (3.5 kDa cut-off) and dialyzed against water to remove excess maleic acid and low molecular weight by-products. The retentate was then removed from the bag and dried at 60° C. to constant weight, to give C16-π-Polymer A dimaleate (1.79 g).

Example 12

Cysteine Adduct of C16-π-Polymer a Dimaleate

Powdered C16-π-Polymer A dimaleate (Example 11) (253 mg) was added to water (5 mL) and the mixture was stirred vigorously. Cysteine (24 mg) and TEMED (30.5 ul) were added to the reaction mixture, and the mixture was stirred at room temperature under an argon atmosphere. The progress of the reaction was monitored by TLC (silica gel plates, n-butanol-acetic acid-water, 3:1:1) with detection with ninhydrin. The reaction mixture showed a ninhydrin-positive spot co-migrating with the polymer. Cysteine also gave a ninhydrin-positive spot, whereas the starting polymer did not give any color with ninhydrin.

3. Use of π Polymers to Solubilize Insoluble or Weakly Soluble Substances

Example 1

Solubilization of Dyes

To 1.0 ml aliquots of a 50 mg/ml aqueous solution of PEG1500-co-succinyl-DTT-bis-C16-amide polymer (C16-Polymer A, Example 1), centrifuged to remove insoluble materials but not otherwise purified, were added excess amounts of the dyes Eosin Y, dichlorofluorescein, and Sudan IV, in separate containers (FlexExcel™ clear polypropylene weigh-boats, WB2.5 size, product of AllExcel, Inc., West Haven, Conn.), and the components were stirred together to form a paste. The container bottoms were then attached to the bottom of a small jewelry ultrasonic cleaner bath using a water-resistant double-stick tape. Just enough water was added to the bath to immerse the weigh boats to about ⅓rd height. Sonication was performed for 15 minutes in steps of 5 minutes. The liquids were transferred to centrifuge tubes and centrifuged twice for 30 min. in a bench top centrifuge to pellet out undissolved dye. The supernatants were transferred to clean tubes and centrifuged again, to remove entrained solids. Suspensions of same amounts of dyes in same amount of distilled water as the amount of the polymer solution were treated in the same fashion, as controls. The resulting solutions were spotted (25 ul) on TLC plates to form circles from the drops. The intensities of the spots were compared with spots made from standards of dye solutions made in ethanol or ethanol/water to determine approximate concentrations; the spots are shown in FIG. 1. The solubilities of the dyes in water were determined by dissolving appropriate amount of the dye in 11 or more deionized water (unbuffered) at room temperature, and adding (i.e. titrating with) further water as necessary to obtain saturated solutions.

The concentration of Sudan IV in 50 mg/ml polymer was approximately 0.2 mg/ml, as opposed to 0.000 mg/ml in $H_2O$ (Sudan IV is insoluble at neutral pH). The concentration of Dichlorofluorescein was approximately 5 mg/ml in 50 mg/ml polymer, as opposed to 0.010 mg/ml in $H_2O$. The concentration of Eosin Y in 50 mg/ml polymer was approximately 5 mg/ml, as opposed to 0.007 mg/ml in $H_2O$. The payload ratios (amount of drug per unit amount of polymer, g/g) were calculated to be approximately 1:250 for Sudan IV, 1:10 for dichlorofluorescein and 1:10 for Eosin Y.

The payload ratios of 1:10 for polar compounds that resemble pharmaceutically active substances in physico-chemical properties are higher than those generally attainable with liposomes, cyclodextrins, Cremophor™, or detergent or other solubilizing systems. Eosin Y is a photoactivable singlet oxygen generator with a very high efficiency, and such concentrated solutions of Eosin Y as are made with the polymer of Example 1 may be expected to be pharmacologically active as photoactivable cytotoxic agents.

The change in fluorescence spectrum of dichlorofluorescein in the polymer solution (reddish yellow/orange) over that in water (greenish yellow) was visually noticeable and gives an indication that the dye is not in an aqueous environment, but is encapsulated in the organic environment of the self-assembled polymer particle cores. Indeed, changes in fluorescence spectra have been used as a method of determining changes in the polarity of the microenvironment (e.g. "lipid probes"). The color of the Sudan IV solution in the polymer was reddish brown, as opposed to red in ethanol solution and brown powder when suspended in water. Eosin Y did not show a significant visual shift (pink in water to reddish pink in the polymer solution).

Example 2

Solubilization of Medically Relevant Substances

Purpurin, Amphotericin B, Camptothecin and Doxorubicin were selected as representative sparingly soluble active pharmaceutical ingredients (API). Amphotericin B is used in a liposomal formulation as an injectable antifungal, while Camptothecin and Doxorubicin are anticancer agents. Purpurin is a DNA intercalating dye with potential pharmaceutical utility, and Eosin Y is a photosensitive singlet oxygen reagent with potential use in photodynamic therapy. Each API was solubilized in water with C16-π-Polymer A, C18-π-Polymer B, and/or C16-π-Polymer A-folic acid conjugate (see below). Solubilization was demonstrated by spotting the solubilized API and non-solubilized controls on TLC plates, as described above for the dyes.

Dried polymers were reconstituted with water, with heating, agitation, and sonication as necessary. When the solution was too viscous, it was diluted. C16-π-Polymer A was used at 10% w/v, folated C16-π-Polymer A was used at 5% w/v, and C18-π-Polymer B was used at 2% w/v.

Figure 2:
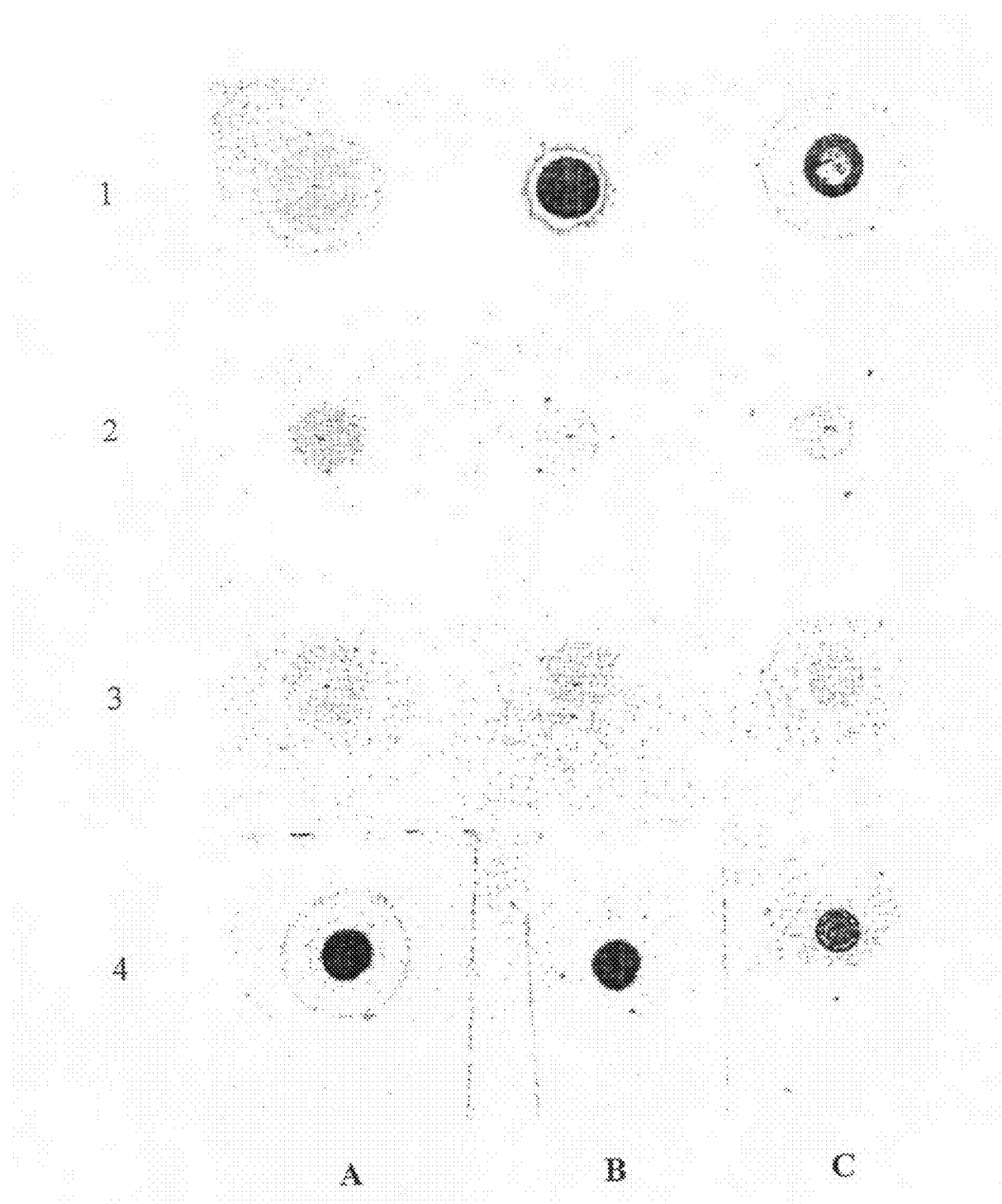
FIG. 2 shows 50 ul samples of saturated solutions of four insoluble drugs (row 1, Purpurin; row 2, Camptothecin; row 3, Amphotericin B; row 4, Doxorubicin) in deionized water, spotted onto a silica get TLC plate. Column A, folated Polymer A; column B, Polymer A, column C, no polymer. Three pencil marks around each spot indicate the extent of spread of solvent on the plate. The central circles in columns A and B are uniformly dispersed into the silica, indicating clear solutions; the central circles in column C consist largely of solid deposits.

Drug substance (20 mg) was added directly to 1 ml of polymer solution, resulting in polymer:API mass ratios of 5:1 for C16-π-Polymer A, 2.5:1 for folated C16-π-Polymer A, and 1:1 for C18-π-Polymer B, except for doxorubicin (see below). The mixtures were sonicated for 1 hr at low power, and then centrifuged twice at 2000×g to remove undissolved solids. The amount of pelleted solids was not significant. Spotting the solutions on a silica gel TLC plate showed that the drugs were solubilized, with migration retarded from the solvent front (FIG. 2).

Doxorubicin hydrochloride was combined with polymers as above at a 10:1 C16-π-Polymer A to doxorubicin hydrochloride mass ratio, or at a 5:1 folated C16-π-Polymer A to doxorubicin mass ratio, followed by addition of sufficient 3M sodium acetate to neutralize the doxorubicin hydrochloride. The mixtures were vigorously shaken for 24 hours and then twice centrifuged at 2000×g to remove undissolved solids. The amount of pelleted solids was not significant.

The mass ratios of solubilized APIs to polymer are shown in Table 1. No attempt was made to maximize the loading of the polymer, therefore these ratios represent lower limits on the amount of API the polymers are capable of carrying into solution.

A 50 ul sample of each solution was spotted on a Baker-flex™ silica gel TLC plate and allowed to spread. The aqueous solution forms an outer boundary of the circle and an inner circle formed by migration of the polymer with encapsulated material (FIG. 2). In all cases, there was very little API in the peripheral fringe of the aqueous-only zone, indicating successful solubilization and minimal leakage of the encapsulated material.

TABLE 1

Solubilization of APIs

| | Polymer: Substrate Mass Ratios | | |
|---|---|---|---|
| | C16-π-Polymer A 10% w/v | Folated C16-π-Polymer A 5% w/v | C18-π-Polymer B 2% w/v |
| Purpurin | 5:1 | 2.5:1 | not done |
| Camptothecin | 5:1 | 2.5:1 | not done |
| Amphotericin B | 5:1 | 2.5:1 | not done |
| Doxorubicin | 10:1 | 5:1 | not done |
| Eosin Y | not done | not done | 1:1 |

4. Biocompatibility of π Polymers

Example 1

Suitability for Topical Emollients, Creams or Pastes

A concentrated oily wax of the polymer of Example 1 was rubbed on the inner wrist skin by the inventor and observed for uptake. The material appeared to be absorbed similarly to pharmacological waxy creams, with slight softening of the area. No immediate or delayed allergic responses, such as reddening, rash, or itching, were observed upon this single topical application.

Many of these polymers are hygroscopic waxes at room temperature, with an expected mp of about 45° C. to 60° C. or greater, depending upon the composition. Polymers made with lower MW PEG's may even be liquid at room temperature. Some polymers may be solid at room temperature, melting at body temperature. Thus the properties of these it polymers make them excellent substrates for making lotions, creams, ointments, emollients, and other delivery forms, either by themselves, or in mixture with various substances, including active pharmaceutical agents.

Example 2

Suitability for Parenteral Administration

An aqueous solution of the polymer of Example 1 was prepared in phosphate-buffered saline and then filtered into sterile tubes through 0.22 um filters.

A maximum tolerated dose protocol was employed, wherein CD-1 mice were subjected to a dose of 10 ml per kg body weight tail vein injection of up to 5% w/v aqueous solution of the polymer. The mice were observed for 12 hours continuously and every 2 hr thereafter until 48 to 72 hrs, depending upon the group. Blood samples were taken and analyzed. Some mice were sacrificed and first examined for gross histology. Microscopic histology was then performed on selected sections.

No observable differences were found in the blood chemistry between the control mice and the treated mice. No observable differences or lesions were found compared to control animals in the gross histology of various organs including heart, lungs, kidneys, spleen, liver, intestines, stomach, bladder, skin, muscles, bones, brain, and lymph nodes. Multiple specimens from different groups of animals were studied with the same results being observed. No observable differences were found in cellular tissue structure of examined tissues. Some of the kidneys showed some casting that diminished with exposure time to the polymer. This implies that the casting is a temporary phase and as the time progresses it will become normal.

It is concluded that the polymer is safe for medical use as a pharmaceutical agent in injectable preparations and other parenteral formulations. It is reasonable to expect that the polymer is safe in oral solutions, caplets, and tablets, nasal spray, oral/bronchial aerosols, sublingual, skin cream/lotion/patch, eyedrops, other topical routes, and other routes of administration.

5. Attachment of Targeting Moieties to π-Polymers

Example 1

Attachment of Galactosamine to C-16 π-Polymer B Via Amide Bond Formation

Galactosamine (GA) targets the hepatic asialoglycoprotein receptor (ASGPR), and polymers bearing covalently-bonded glactosamine are delivered to the liver; see L. Seymour et al., "Hepatic Drug Targeting: Phase I Evaluation of Polymer-Bound Doxorubicin" *J. Clin. Oncology*, 20(6): 1668-1676 (2002) and references therein.

C16-π-Polymer B (Example 10 in synthetic method section above) (461 mg, 0.2 mmols equivalent COOH per repeating unit) was dispersed in 14 mL water, and to this dispersion was added EDC HCl (0.485 mmols) and N-hydroxysuccinimide (0.464 mmols). The mixture was stirred at ambient temperature for 15 minutes and a solution of galactosamine HCl (0.386 mmols) and TEMED (0.387 mmols) in 1 ml water was added. The solution was stirred and the reaction was followed by TLC on silica gel and development in 1-butanol-acetic acid-water (3:1:1). An additional amount of TEMED (0.079 mmols), NHS (0.078 mmols) and EDC HCl (0.193 mmols) were added to force the reaction to completion. When TLC showed a steady state with respect to consumption of GA, the reaction mixture was dialyzed (3500 Da cut-off membrane) against 3×1000 ml deionized water to remove the low molecular weight reactants and by-products. The retentate was removed and dried at 60° C. to constant weight (348 mg).

TLC of the product showed no free GA (ninhydrin negative). A sample of the product was hydrolyzed with 6 N HCl at 100° C. to hydrolyze bound GA. TLC analysis showed the presence of GA (ninhydrin positive) at the same Rf as reference GA.

Example 2

Attachment of Folic Acid to C18-π-Polymer A

BDDC (2.44 g, 8.56 mmols) was weighed out in a 125 mL round-bottom flask flushed with argon (BDDC is very viscous with honey like consistency and difficult to handle). C18-π-Polymer A (10 g, 4.28 mmols) was added to the flask, the mixture was heated to 70° C., and the reactants were stirred together for about 30 minutes. Folic acid (3 g) was added followed by sufficient THF to make stirring possible. The reactants were stirred at 40-70° C. overnight, protected from moisture. The THF was then allowed to evaporate and water (80 mL) was added, and the mixture was stirred at 50° C. for an additional 2 h. After cooling to room temperature, the mixture was transferred to a section of dialysis tubing with a 3500 Dalton cut off, and dialyzed against 0.1 N HCl (2×2000 ml), water (2000 ml), 5% sodium carbonate (2×2000 ml) and water (4×2000 ml), to remove unreacted reagents and by-products. The bright yellow-orange retentate was removed. A portion was evaporated to constant weight to determine the solid concentration, and was used for the solubilization experiments described above.

Example 3

Attachment of N-acetyl neuraminic acid (NANA) to C16-π-Polymer B

Neuraminic acid derivatives are expected to be targeting moieties for influenza viruses because of the hemagglutinin and neuraminidase coat proteins, both of which are known to bind to sialic acid.

BDDC (2.44 g, 8.56 mmols) and C18-π-Polymer A (10 g, 4.28 mmols) are combined and heated to 70° C., and stirred together under argon for about 30 minutes. N-acetyl neuraminic acid (3 g) is added, followed by THF as necessary to maintain fluidity. The reactants are stirred at 40-70° C. overnight, protected from moisture. Water (80 mL) is added, and the mixture is stirred at 50° C. for an additional 2 h. After cooling to room temperature, the mixture is dialyzed against 0.1 N HCl, 5% NaHCO₃, and water (2×2000 ml each) with a 3.5 kDa cutoff membrane.

Example 4

Attachment of β-O-methyl Neuraminic Acid (MNA) to C16-π-Polymer B

C16-π-Polymer B, 43 micromoles COOH basis, in 1 ml water, and neuraminic acid β-methyl glycoside (Toronto Research Chemicals), 40 micromoles, were mixed together, and 40 micromoles NHS in 0.1 ml water was added, followed by 40 micromoles EDC hydrochloride in 0.1 ml water. The reaction mixture was shaken at ambient temperature for 48 hours, and analyzed by TLC on silica gel with isopropanol-ethy acetate-water (4:3:2). Detection with 0.2% orcinol in 70% sulfuric acid, at 130° C., does not generate a color reaction with the starting polymer, but TLC of the reaction mixture gave a purple spot co-migrating with the polymer.

Example 5

Attachment of Zanamivir to C16-π-Polymer B

Zanamivir (GG167) is a potent inhibitor of viral neuraminidase, and polymers bearing this molecule as a multivalent ligand are inhibitors of influenza virus replication.

C16-π-Polymer B (920 mg) is dispersed in 30 mL water, and to this is added EDC HCl (1.2 mmol) and N-hydroxysuccinimide (1.1 mmol). The mixture is stirred at ambient temperature for 20 minutes, and a solution of the trifluoroacetic acid salt of 5-acetamido-7-(6'-aminohexyl)-carbamyloxy-4-guanidino-2,3,4,5-tetradeoxy-D-glycero-D-galacto-non-2-enopyranosonic acid (U.S. Pat. Nos. 6,242,582 and 6,680,054) (0.39 g, 0.67 mmol) and TEMED (0.67 mmols) in 1 ml water is added. The solution is stirred at room temperature, and the reaction is followed by TLC. The reaction mixture is dialyzed (3500 kDa cut-off membrane) against 3×1000 ml deionized water to remove the low molecular weight reactants and by-products. The retentate is removed and dried at 60° C. to constant weight. The level of sugar incorporation may be determined by a colorimetric assay for the guanidine group (*Can. J. Chem.*, 36:1541 (1958)). A neuraminidase assay may be carried out following the procedure of Potier et al, *Anal. Biochem.*, 29 287 (1979).

Example 6

Attachment of Fab Fragment to C16-π-Polymer A Dimaleate

A single-chain variable fragment antibody (scFv) directed against the surface glycoprotein high-molecular-weight melanoma-associated antigen (HMW-MAA) targets melanoma cells; see F. Martin et al., *J. Virology*, 73:6923-6929 (1999).

Disulfide bonds in this antibody fragment are reduced with Immobilized TCEP Disulfide Reducing Gel (Pierce Biotechnology, Rockford, Ill.) according to the manufacturer's protocol, and reacted with C16-π-Polymer A dimaleate by the method of Example 12 in the Synthetic Methods section.

We claim:

1. A comb polymer consisting essentially of the following structure:

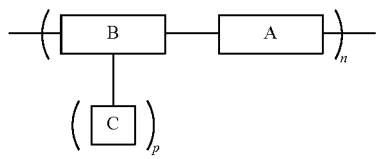

comprising a backbone formed of alternating branch-point moieties B and hydrophilic, water-soluble polymer blocks A; and having hydrophobic side chains C attached to the branch-point moieties, wherein each side chain C is independently selected from the group consisting of linear hydrocarbons optionally substituted with one or more hydrophilic substituents, polycyclic hydrocarbons optionally substituted with one or more hydrophilic substituents, hydrophobic amino acids, peptides and polymers; wherein n ranges from 3 to about 100; and wherein, on average, $1 < p \leq 4$.

2. The polymer of claim 1, wherein, on average, p ranges from about 2 up to 4.

3. The polymer of claim 1, wherein, on average, $1.5 \leq p \leq 2$.

4. A polymer according to claim 1, further comprising one or more reactive functional groups X attached to each branch-point moiety, and consisting essentially of the following structure:

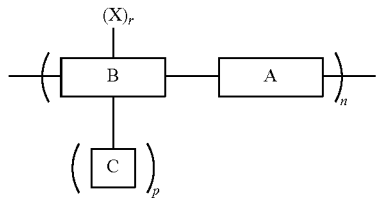

wherein, on average, r ranges from about 1 to about 4.

5. The polymer of any of claims 1-4, wherein the water-soluble polymer block A is selected from the group consisting of poly(ethylene glycol), poly(propylene glycol), poly(ethylene imine), poly(vinyl alcohol), poly(vinylpyrrolidone), and polysaccharides, and copolymers thereof.

6. The polymer of claim 5, wherein the polymer block A is selected from the group consisting of poly(ethylene glycol) and poly(propylene glycol), and copolymers thereof.

7. The polymer of claim 6, wherein the polymer block A is poly(ethylene glycol).

8. The polymer of claim 7, wherein the polymer block A has an average length of between 4 and 700 monomer units.

9. The polymer of claim 4, having the structure

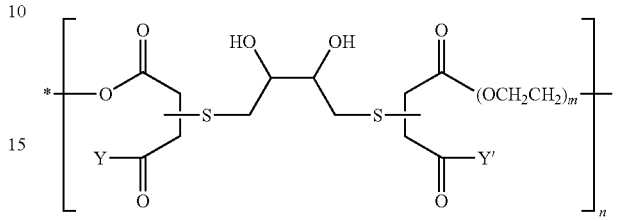

wherein m is 4-700, and Y and Y' are independently selected from the group consisting of R, OR, COOR, SR, NHR, NRR', ONHR, NHOR, NRNH$_2$, NHNHR, NRNHR', and NHNRR', wherein R and R' are independently selected from the group consisting of linear hydrocarbons optionally substituted with one or more hydrophilic substituents, polycyclic hydrocarbons optionally substituted with one or more hydrophilic substituents, hydrophobic amino acids, peptides and polymers.

10. The polymer of claim 4, having the structure

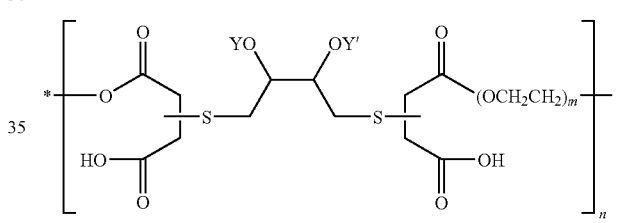

wherein m is 4-700, and Y and Y' are independently selected from the group consisting of R, COR, COOR, CONHR, CONRR', CONHOR, CONRNH$_2$, CONHNHR, CONRNHR', and CONHNRR', wherein R and R' are independently selected from the group consisting of linear hydrocarbons optionally substituted with one or more hydrophilic substituents, polycyclic hydrocarbons optionally substituted with one or more hydrophilic substituents, hydrophobic amino acids, peptides and polymers.

11. The polymer of claim 4, having the structure

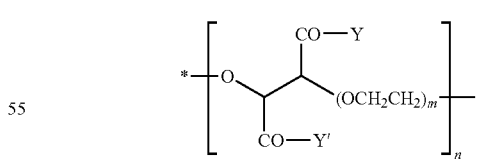

wherein m is 4-700, and Y and Y' are independently selected from the group consisting of R, OR, COOR, SR, NHR, NRR', ONHR, NHOR, NRNH$_2$, NHNHR, NRNHR', and NHNRR', wherein R and R' are independently selected from the group consisting of linear hydrocarbons optionally substituted with one or more hydrophilic substituents, polycyclic hydrocarbons optionally substituted with one or more hydrophilic substituents, hydrophobic amino acids, peptides and polymers.

12. The polymer of claim 3, having the structure

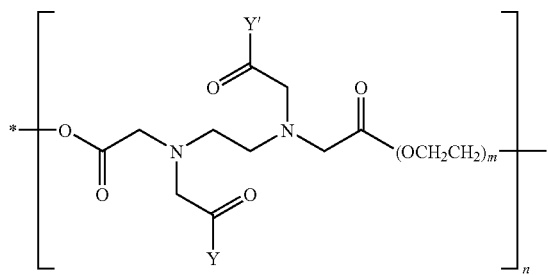

wherein m is 4-700, and Y and Y' are independently selected from the group consisting of R, OR, COOR, SR, NHR, NRR', ONHR, NHOR, NRNH$_2$, NHNHR, NRNHR', and NHNRR', wherein R and R' are independently selected from the group consisting of linear hydrocarbons optionally substituted with one or more hydrophilic substituents, polycyclic hydrocarbons optionally substituted with one or more hydrophilic substituents, hydrophobic amino acids, peptides and polymers.

13. The polymer of claim 3, having the structure

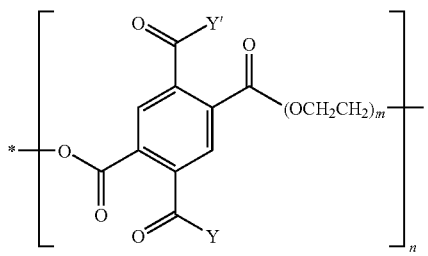

wherein m is 4-700, and Y and Y' are independently selected from the group consisting of R, OR, COOR, SR, NHR, NRR', ONHR, NHOR, NRNH$_2$, NHNHR, NRNHR', and NHNRR', wherein R and R' are independently selected from the group consisting of linear hydrocarbons optionally substituted with one or more hydrophilic substituents, polycyclic hydrocarbons optionally substituted with one or more hydrophilic substituents, hydrophobic amino acids, peptides and polymers.

14. The polymer of claim 3, having the structure

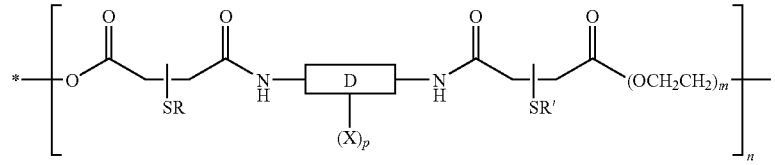

wherein the moiety D is derived from a diamine having the general structure

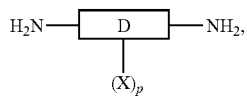

each X is independently a reactive functional group, p is 0-4, and m is 4-700; and wherein R and R' are independently selected from the group consisting of linear hydrocarbons optionally substituted with one or more hydrophilic substituents, polycyclic hydrocarbons optionally substituted with one or more hydrophilic substituents, hydrophobic amino acids, peptides and polymers.

15. The polymer of claim 4, having the structure

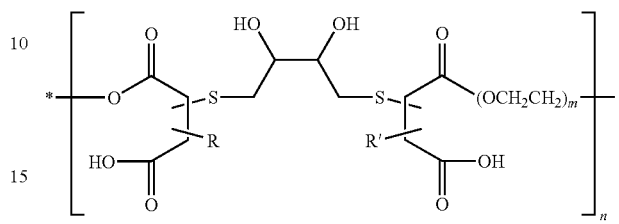

wherein m is 4-700, and R and R' are independently selected from the group consisting of linear hydrocarbons optionally substituted with one or more hydrophilic substituents, polycyclic hydrocarbons optionally substituted with one or more hydrophilic substituents, hydrophobic amino acids, peptides and polymers.

16. The polymer of claim 4, having the structure

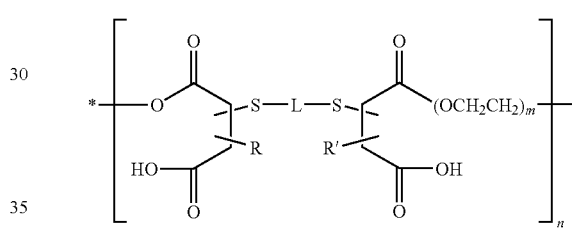

wherein m is 4-700, L is phenylene, $C_2$-$C_6$ alkylene, or benzenedimethylene, and R and R' are independently selected from the group consisting of linear hydrocarbons optionally substituted with one or more hydrophilic substituents, polycyclic hydrocarbons optionally substituted with one or more hydrophilic substituents, hydrophobic amino acids, peptides and polymers.

17. The composition resulting from the chemical reaction of polyethylene glycol and maleic anhydride, resulting in the substantially complete esterification of the terminal hydroxyl groups of the polyethylene glycol by the maleic anhydride, and chemical reaction of the resulting material with dithiothreitol.

18. The composition resulting from the chemical reaction of polypropylene glycol and maleic anhydride, resulting in the substantially complete esterification of the terminal hydroxyl groups of the polypropylene glycol by the maleic anhydride, and chemical reaction of the resulting material with dithiothreitol.

19. A polymer having the structure

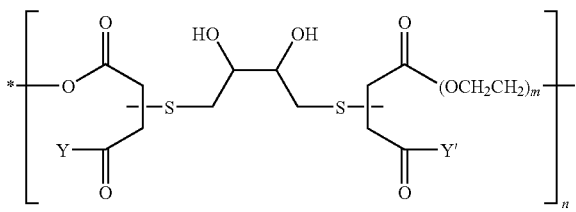

wherein m is 4 to about 700 and n is 3 to about 100, and wherein, in each occurrence of the monomer unit having the structure shown, Y and Y' are independently selected from the group consisting of OH, COOH, SH, NH$_2$, NHR, ONH$_2$, NHOH, NHNH$_2$, and NRNH$_2$, wherein R is selected from the group consisting of C$_1$ to C$_5$ alkyl and (CH$_2$)$_k$OH, (CH$_2$)$_k$COOH, (CH$_2$)$_k$SH, (CH$_2$)$_k$NH$_2$, (CH$_2$)$_k$ONH$_2$, (CH$_2$)$_k$NHOH, and (CH$_2$)$_k$NHNH$_2$, where k is from 2 to 5.

20. A polymer having the structure

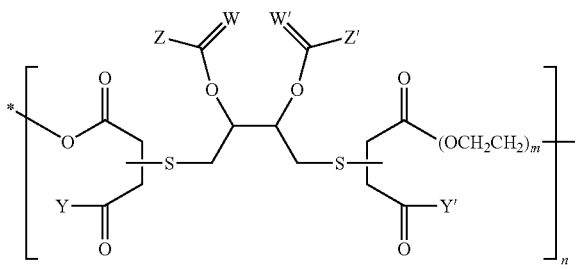

wherein m is 4 to about 700 and n is 3 to about 100, and wherein, in each occurrence of the monomer unit having the structure shown, Y and Y' are independently selected from the group consisting of OH, COOH, SH, NH$_2$, NHR, ONH$_2$, NHOH, NRNH$_2$, and NRNH$_2$, wherein R is selected from the group consisting of C$_1$ to C$_5$ alkyl and (CH$_2$)$_k$OH, (CH$_2$)$_k$COOH, (CH$_2$)$_k$SH, (CH$_2$)$_k$NH$_2$, (CH$_2$)$_k$ONH$_2$, (CH$_2$)$_k$NHOH, and (CH$_2$)$_k$NHNH$_2$, where k is from 2 to 5; W and W' are independently O or H$_2$, and wherein, in each occurrence of the monomer unit, Z and Z' are independently selected from the group consisting of linear hydrocarbons optionally substituted with one or more hydrophilic substituents, polycyclic hydrocarbons optionally substituted with one or more hydrophilic substituents, hydrophobic amino acids, peptides and polymers.

21. A polymer having the structure

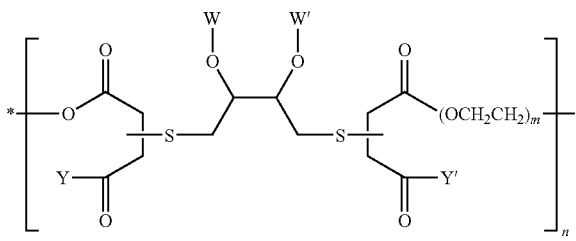

wherein m is 4-700, and Y and Y' are independently selected from the group consisting of R, OR, COOR, SR, NHR, NRR', ONHR, NHOR, NRNH$_2$, NHNHR, NRNHR', and NHNRR', wherein R and R' are independently selected from the group consisting of linear hydrocarbons optionally substituted with one or more hydrophilic substituents, polycyclic hydrocarbons optionally substituted with one or more hydrophilic substituents, hydrophobic amino acids, peptides and polymers; and wherein, in each occurrence of the monomer unit, W and W' are independently selected from the group consisting of H, —COCH=CH$_2$, —COC(CH$_3$)=CH$_2$, COCH=CHCO$_2$H, and —COC(CH$_3$)=CHCO$_2$H.

22. A pharmaceutical composition comprising a polymer according to any of claims 1-9, and further comprising an effective amount of a pharmacologically active agent.

23. A method of increasing the solubility of a substance in an aqueous solvent, which comprises contacting the substance with a polymer according to claim 1 or claim 2 so as to form a water-soluble complex of the substance and the polymer.

24. A method of increasing the solubility of a substance in a non-aqueous solvent, which comprises contacting the substance with a polymer according to claim 1 or claim 2 so as to form a complex of the substance and the polymer that is soluble in the non-aqueous solvent.

25. The method of claim 23, wherein the substance is selected from the group consisting of vitamins, nutrients, drugs, dyes, nucleic acid complexes, and imaging agents.

26. The method of claim 25, wherein the substance is a drug.

27. A method of inducing binding affinity for a biological target in a polymer according to claim 4, comprising the step of attaching a targeting moiety to one or more of the reactive functional groups X present on the polymer.

28. The method of claim 27, wherein the biological target is the surface of a cell or virus.

29. The method of claim 28, wherein the targeting moiety is selected from the group consisting of receptor-specific ligands, antibodies, antibody fragments, peptides comprising an RGD amino acid sequence, peptides comprising a YISRG motif, growth factors, as sialic acid derivatives, N-acetylneuraminic acid derivatives; folate, methotrexate, pteroic acid, estradiol, estratriol, testosternone, mannose-6-phosphate, sugars, vitamins, tryptophan, aminoalkyladamantanes, Fuzeon™, PRO-542, BMS-488043, sialic acid, 2-deoxy-2,3-didehydro-N-acetylneuraminic acid, 4-guanidino-Neu5Ac2en (zanamivir), oseltamivir, and RWJ-270201.

30. The method of claim 29, wherein the targeting moiety is a monoclonal antibody or an antibody fragment.

31. The method of claim 24, wherein the substance is selected from the group consisting of vitamins, nutrients, drugs, dyes, nucleic acid complexes, and imaging agents.

32. The method of claim 31, wherein the substance is a drug.

* * * * *